US008825173B2

(12) United States Patent
Forsell

(10) Patent No.: US 8,825,173 B2
(45) Date of Patent: Sep. 2, 2014

(54) METHOD AND APPARATUS FOR SUPPLYING ENERGY TO A MEDICAL DEVICE

(76) Inventor: Peter Forsell, Zug (CH)

( * ) Notice: Subject to any disclaimer, the term of this patent is extended or adjusted under 35 U.S.C. 154(b) by 219 days.

(21) Appl. No.: 12/682,477

(22) PCT Filed: Oct. 10, 2008

(86) PCT No.: PCT/SE2008/000585
§ 371 (c)(1),
(2), (4) Date: Apr. 9, 2010

(87) PCT Pub. No.: WO2009/051541
PCT Pub. Date: Apr. 23, 2009

(65) Prior Publication Data
US 2010/0211133 A1    Aug. 19, 2010

Related U.S. Application Data

(60) Provisional application No. 60/960,832, filed on Oct. 16, 2007, provisional application No. 60/960,861, filed on Oct. 17, 2007.

(51) Int. Cl.
*A61N 1/00* (2006.01)
*A61N 1/39* (2006.01)
*H02J 5/00* (2006.01)
*A61N 1/08* (2006.01)
*A61N 1/378* (2006.01)
*H02J 7/02* (2006.01)

(52) U.S. Cl.
CPC ......... *H02J 5/005* (2013.01); *A61F 2250/0001* (2013.01); *H02J 7/025* (2013.01); *A61B 2560/0214* (2013.01); *A61N 1/08* (2013.01); *A61N 1/3787* (2013.01)
USPC ............ 607/61; 607/1; 607/2; 607/9; 607/30; 607/31; 607/32; 607/33; 607/34

(58) Field of Classification Search
CPC ... A61N 1/08; A61N 1/37252; A61N 1/3787; A61N 1/37211; A61N 1/40; H02J 7/025
USPC ..................... 607/1, 2, 9, 30–34, 61
See application file for complete search history.

(56) References Cited

U.S. PATENT DOCUMENTS 3,677,251 A * 7/1972 Bowers ............................ 607/9
4,387,714 A    6/1983 Geddes et al.
(Continued)

FOREIGN PATENT DOCUMENTS

EP          1 609 501        12/2005

OTHER PUBLICATIONS

International Search Report for PCT/SE2008/000585, mailed Mar. 2, 2009.

(Continued)

*Primary Examiner* — Niketa Patel
*Assistant Examiner* — Lindsey G Hankins
(74) *Attorney, Agent, or Firm* — Nixon & Vanderhye PC

(57) ABSTRACT

For supplying energy to a medical implant (100) in a patient's body a receiver (102) cooperates with an external energizer (104) so that energy is wirelessly transferred. A feedback communication system (109) sends feedback information from the receiver to the energizer, the feedback information being related to the transfer of energy to the receiver. The feedback communication system communicates using the patient's body as an electrical signal line. In particular, the communication path between the receiver and the external energizer can be established using a capacitive coupling, i.e. the feedback information can be capacitively transferred over a capacitor having parts outside and inside the patient's body. An energy balance between the amount of energy received in the receiver and the energy used by the medical implant can be followed over time, and then the feedback information is related to the energy balance.

19 Claims, 13 Drawing Sheets

(56) References Cited

U.S. PATENT DOCUMENTS

| | | | |
|---|---|---|---|
| 5,411,537 A * | 5/1995 | Munshi et al. | 607/33 |
| 5,702,431 A | 12/1997 | Wang et al. | |
| 6,445,955 B1 * | 9/2002 | Michelson et al. | 607/46 |
| 2004/0039423 A1 | 2/2004 | Dolgin | |
| 2004/0064166 A1 * | 4/2004 | Thompson et al. | 607/60 |
| 2005/0288740 A1 | 12/2005 | Hassler, Jr. et al. | |
| 2006/0271128 A1 * | 11/2006 | Keuninckx | 607/60 |
| 2007/0156204 A1 | 7/2007 | Denker et al. | |
| 2010/0211134 A1 | 8/2010 | Forsell | |
| 2010/0217352 A1 | 8/2010 | Forsell | |
| 2010/0217353 A1 | 8/2010 | Forsell | |
| 2010/0222848 A1 | 9/2010 | Forsell | |
| 2010/0222849 A1 | 9/2010 | Forsell | |
| 2010/0234922 A1 | 9/2010 | Forsell | |
| 2011/0193688 A1 | 8/2011 | Forsell | |
| 2011/0196452 A1 | 8/2011 | Forsell | |
| 2011/0201276 A1 | 8/2011 | Forsell | |
| 2011/0278948 A1 | 11/2011 | Forsell | |
| 2011/0301668 A1 | 12/2011 | Forsell | |
| 2012/0112556 A1 | 5/2012 | Forsell | |
| 2012/0119700 A1 | 5/2012 | Forsell | |

OTHER PUBLICATIONS

Written Opinion of the International Searching Authority for PCT/SE2008/000585, mailed Mar. 2, 2009.
U.S. Appl. No. 13/384,387 (Forsell) filed Jan. 17, 2012.
U.S. Appl. No. 13/384,039 (Forsell) filed Jan. 13, 2012.
U.S. Appl. No. 13/130,648 (Forsell) filed Aug. 3, 2011.
U.S. Appl. No. 13/130,634 (Forsell) filed Aug. 3, 2011.
U.S. Appl. No. 13/123,638 (Forsell) filed Apr. 11, 2011.
U.S. Appl. No. 13/123,252 (Forsell) filed Apr. 8, 2011.
U.S. Appl. No. 13/123,168 (Forsell) filed Apr. 7, 2011.
U.S. Appl. No. 12/738,182 (Forsell) filed Apr. 15, 2010.
U.S. Appl. No. 12/682,835 (Forsell) filed Apr. 13, 2010.
U.S. Appl. No. 12/682,831 (Forsell) filed Apr. 13, 2010.
U.S. Appl. No. 12/682,404 (Forsell) filed Apr. 9, 2010.
U.S. Appl. No. 12/682,336 (Forsell) filed Apr. 9, 2010.
U.S. Appl. No. 12/682,327 (Forsell) filed Apr. 9, 2010.
U.S. Appl. No. 13/905,384 (Forsell) filed May 30, 2013.
U.S. Appl. No. 14/107,255 (Forsell) filed Dec. 16, 2013.

* cited by examiner

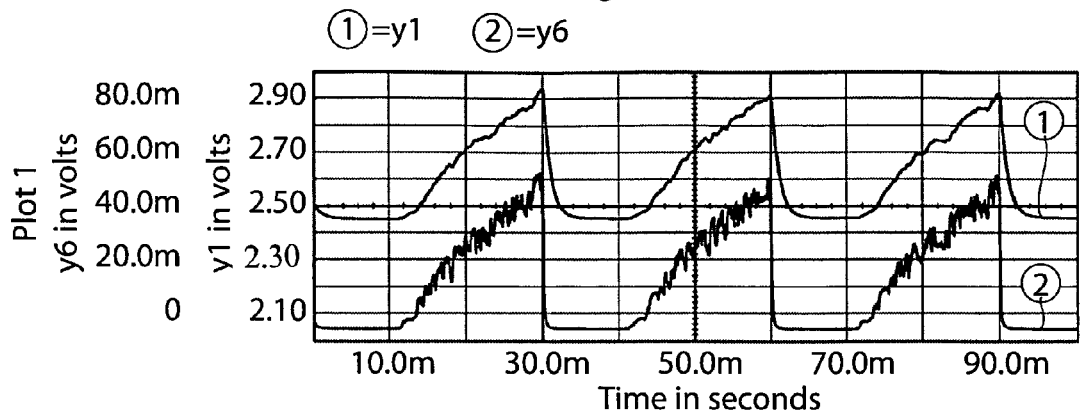
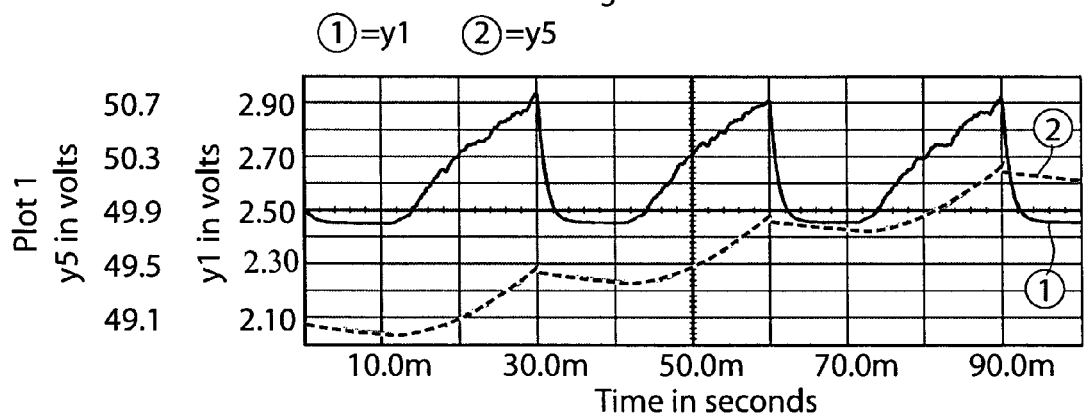
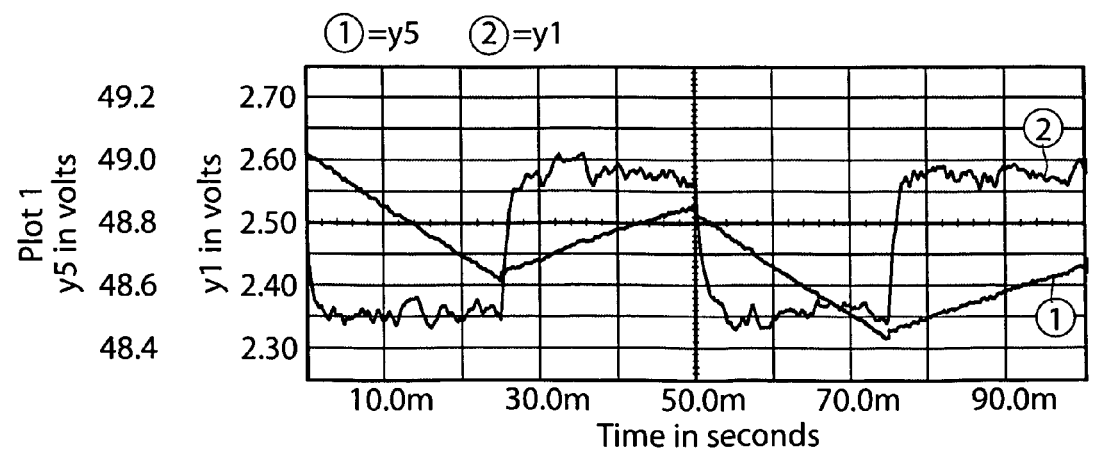

METHOD AND APPARATUS FOR SUPPLYING ENERGY TO A MEDICAL DEVICE

This application is the U.S. national phase of International Application No. PCT/SE2008/000585 filed 10 Oct. 2008, which designated the U.S. and claims the benefit of U.S. Provisional Appln. No. 60/960,832 filed 16 Oct. 2007, and U.S. Provisional Appln. No. 60/960,861 filed 17 Oct. 2007, the entire contents of each of which are hereby incorporated by reference.

TECHNICAL FIELD

The present invention relates generally to a method and apparatus for wirelessly supplying power or energy to a medical device implanted in a person's or patient's body and, in particular, to controlling the amount of energy transferred from an energy source outside the person's or patient's body to an energy receiver inside the person's or patient's body.

BACKGROUND

A medical device, designed to be subcutaneously implanted, may include e.g. electronic circuits and/or some other electric device and hence it needs, like any other similar device, electric power for its operation. Examples of such medical devices include e.g. electrical and mechanical stimulators, motors, pumps, valves and constriction devices that can support, stimulate or control various body functions of the person in which the medical device is implanted.

Electric power to a medical device implanted in a person's body can as conventional be supplied from an implanted electrical energy storage such as one or more electrochemical cells. Electric power to devices located inside a person's body can also be supplied from outside the body using wireless energy transfer, for example supplying electric power using electrical induction. In wireless energy transfer any needed amount of electrical power can be supplied intermittently or continuously, without requiring repeated surgical operations. The wirelessly supplied power can be used to directly operate an implanted medical device or to charge an implanted electrical energy storage.

A device suited to be implanted can also require electrical signals in order to generally control its operation and its functions such as, in a simple case, to start or stop the operation of the device. For more complicated devices or devices having more complicated functions, the device could also be required to provide feedback, i.e. signals representing the current state of the device or its function or e.g. some value sensed by the implanted device. Such signals can be exchanged with an external device, e.g. a controller. Then, the signals can also be wirelessly transferred.

Wireless supply of power and wireless exchange of signals have for a medical implant the obvious advantage that no electrical line or cable extending through the skin of the person having the implant is required.

Wireless communication of signals of course also requires electrical power. This is of special importance considering implanted devices and the communication should be designed to require as small electrical power and energy as possible from the implants.

Thus, an external energy source can wirelessly transfer energy to an implanted internal power receiver that is located inside a patient's body and is connected to a medical device for supplying power thereto. So-called TET (Transcutaneous Energy Transfer) devices are known in the art that can wirelessly transfer energy in this manner.

A TET device typically comprises an external energy source including a primary coil adapted to wirelessly transfer any amount of electrical energy by electric induction, by inducing a voltage in a secondary coil of an internal energy receiver which may be implanted immediately inside a person's skin. The efficiency of the inductive power transfer is higher when the primary coil is positioned closer to the secondary coil and when the primary coil is more aligned with the secondary coil, i.e. when a symmetry axis of the primary coil is made more parallel to that of the secondary coil.

Typically, the amount of energy required to operate an implanted medical device may vary over time depending on the operational characteristics of the device. For example, the device may be designed to be switched on and off at certain intervals, or otherwise change its behaviour, in order to provide a suitable electrical or mechanical stimulation, or the like. Such operational variations will naturally result in corresponding variations with respect to the amount of required energy.

Furthermore, the position of the external energy source in relation to the implanted internal energy receiver affects the efficiency of the wireless energy transfer, which as indicated above highly depends on the distance and relative angle between the source and the receiver. For example, when primary and secondary coils are used, changes in coil spacing result in a corresponding variation of the induced voltage. During operation of the medical device, the patient's movements will typically change the relative spacing of the external source and the internal receiver arbitrarily such that the transfer efficiency will have a corresponding large variation.

If the efficiency of the wireless energy transfer becomes low, the amount of energy supplied to the medical device may be insufficient for operating the device properly, so that its action must be momentarily stopped. It may of course interfere with the intended medical effect of the medical device.

On the other hand, the energy supplied to the medical device may also increase drastically, if the relative positions of the external source and the internal receiver change in a way that unintentionally increases the efficiency of the wireless energy transfer. This situation can cause severe problems since the implant cannot "consume" the suddenly very high amount of supplied energy. Unused excessive energy must be absorbed in some way, resulting in the generation of heat, which is highly undesirable. Hence, if excessive energy is transferred from the external energy source to the internal energy receiver, the temperature of the implant will increase, which may damage the surrounding body tissues or otherwise have a negative effect on the body functions. It is generally considered that the temperature in the body should not increase more than three degrees to avoid such problems.

It is thus highly desirable to always supply the correct or appropriate amount of energy to an implanted medical device, in order to ensure a proper operation and/or to avoid an increase of temperature. Various methods are known for controlling the amount of transferred energy in response to different conditions in the receiving implanted device. However, the presently available solutions for controlling the wireless transfer of energy to implanted medical devices are lacking in precision in this respect.

For example, U.S. Pat. No. 5,995,874 discloses a TET system in which the amount of energy transferred from a primary coil is controlled in response to an indication of measured characteristics of a secondary coil, such as load current and voltage. The transferred energy can be controlled by varying the current and voltage in the primary coil, the frequency of the alternating current or the coil dimensions. In particular, a change is effected in the saturation point of the magnetic field between the coils, in order to adjust the power transfer efficiency. However, it is not likely that this solution will work well in practice, since a saturation point in the human tissue would not occur, given the magnetic field levels that can be possibly used. Moreover, if the energy transfer rate must be increased considerably, e.g. to compensate for losses due to variations in alignment and/or spacing between the coils, the relatively high electric and magnetic field may be damaging or unhealthy or at least unpleasant to the patient, as is well known.

An efficient system and an efficient method are thus needed for accurately controlling the amount of energy wirelessly transferred to an implanted medical device to ensure a proper operation thereof. Moreover, excessive energy transfer resulting in a raised temperature at the medical device, and/or power surges in the energy transfer should be avoided, in order to avoid tissue damages and other unhealthy or unpleasant consequences for the patient.

SUMMARY

Generally, a method is provided for controlling wireless transfer of energy to an electrically operable medical device implanted in the body of a mammal patient. The energy is wirelessly transferred from an external energy source located outside the patient's body and is received by an internal energy receiver located inside the patient's body. The internal energy receiver is connected to the medical device and supplies received energy directly or indirectly thereto. In order to control the energy transfer, a feedback control signal is transferred using a feedback communication system having an internal communication unit device located inside the patient's body and an external communication unit located outside the patient's body. The feedback control signal reflects a required amount of energy for operating the medical device and is used for controlling the wireless energy transfer from the external energy source.

Generally also, in the same way an apparatus is provided for controlling wireless transfer energy to an electrically operable medical device implanted in a mammal patient's body. The apparatus comprises an external energy source, an internal energy receiver and a feedback communication system, which perform the respective functions described above.

In the feedback communication system, generally the external communication unit has a part adapted to be in contact with or be placed in a close vicinity of the patient's body when in use. The external communication unit and the internal communication unit communicates with each other using a communication path, a part of which uses or includes the patient's body for the communication of information.

In particular, the feedback communication system is based on the realization that by using the patient's body as a communication medium and measuring the electric potential in different places, communication between a medical implant and a communication unit outside the patient's body can be established with a minimum of electric current flowing through the patient's body. In particular, a portion of the patient's body is used as part of a capacitor. Generally then, the internal communication unit comprises a communication receiver, transmitter or transceiver that includes one part of a capacitive energy storage. The communicating of information using the capacitive coupling includes that an electrical current is injected into or is drawn from the capacitive energy storage:

In the communication system, the information can e.g. be represented as variations of the derivative of the voltage over the capacitive energy storage, i.e. as transitions in the voltage level.

The information may be coded according to the Manchester system.

Dual frequency communication can be used.

The general method and apparatus may be implemented according to different embodiments and features as follows.

In one embodiment, an internal control unit in the apparatus determines an energy balance between the energy received by the internal energy receiver and the energy used for the medical device, and the feedback control signal comprises information on the determined energy balance. The wireless transfer of energy from the external energy source is controlled, such as by an external control unit, based on the determined energy balance, as given by the feedback control signal.

In another embodiment, the feedback control signal comprises information about measurements relating to characteristics of the medical device. In that case, an external control unit is used to determine an energy balance between the energy received by the internal energy receiver and the energy used for the medical device based on the feedback control signal, and to control the wireless energy transfer from the external energy source based on the determined energy balance.

Further Embodiments

The wireless energy may be transferred using electric induction between a primary coil in the external energy source and a secondary coil in the internal energy receiver. A change in the energy balance may be detected to control the wireless transfer of energy based on the detected energy balance change. A difference may also be detected between energy received by the internal energy receiver and energy used for the medical device, to control the wireless energy transfer based on the detected energy difference.

When controlling the energy transfer, the amount of wirelessly transferred energy may be decreased if the detected energy balance change implies that the energy balance is increasing, or vice versa. The decrease/increase of wireless energy transfer may further correspond to a detected change rate.

The amount of wirelessly transferred energy may be decreased if the detected energy difference implies that the amount of received energy is larger than the used energy, or vice versa. The decrease/increase of the wireless energy transfer may then correspond to the magnitude of the detected energy difference.

As mentioned above, the energy used for the medical device may be consumed to operate the medical device, and/or stored in at least one energy storage device of the medical device.

In one alternative, substantially all energy used for the medical device is consumed to operate the medical device. In that case, the energy may be consumed after having been stabilized in at least one energy stabilizing unit of the medical device.

In another alternative, substantially all energy used for the medical device is stored in the at least one energy storage device. In yet another alternative, the energy used for the medical device is partly consumed to operate the medical device and is partly stored in the at least one energy storage device.

The energy received by the internal energy receiver may be stabilized by a capacitor, before the energy is supplied, directly or indirectly, to the medical device.

The difference between the total amount of energy received by the internal energy receiver and the total amount of consumed and/or stored energy may be directly or indirectly measured over time, and the energy balance can then be determined based on a detected change in the difference of the total amounts.

The energy received by the internal energy receiver may further be accumulated and stabilized in an energy stabilizing unit, before the energy is supplied to the medical device. In that case, the energy balance may be determined based on a detected change in the amount of consumed and/or stored energy that is followed over time. Furthermore, the change in the amount of consumed and/or stored energy may be detected by determining over time the derivative of a measured electrical parameter related to the amount of consumed and/or stored energy, where the derivative at a first given moment corresponds to the rate of the change at the first given moment, the rate of change including the direction and velocity of the change. The derivative may further be determined based on or as a detected rate of change of the electrical parameter.

The energy received by the internal energy receiver may be supplied to the medical device as at least one constant voltage, wherein the constant voltage is created by a constant voltage circuitry. In that case, the energy may be supplied as at least two different voltages, including the at least one constant voltage.

The energy received by the internal energy receiver may also be supplied to the medical device as at least one constant electric current, wherein the constant electric current is created by a constant current circuitry. In that case, the energy may be supplied as at least two different electric currents including the at least one constant electric current.

The energy balance may also be determined based on a detected difference between the total amount of energy received by the internal energy receiver and the total amount of consumed and/or stored energy, the detected difference being related to the integral over time of at least one measured electrical parameter related to the energy balance. In that case, values of the electrical parameter may be plotted over time as a graph in a parameter-time diagram, and the integral can be determined from the size of the area beneath the plotted graph. The integral of the electrical parameter may relate to the energy balance as an accumulated difference between the total amount of energy received by the internal energy receiver and the total amount of consumed and/or stored energy.

The energy storage device comprised in or connected to the medical device may include at least one of a rechargeable battery, an accumulator or a capacitor. The energy stabilizing unit may include at least one of: an accumulator, a capacitor or a semiconductor adapted to stabilize the received energy.

When the energy received by the internal energy receiver is accumulated and stabilized in an energy stabilizing unit before energy is supplied to the medical device and/or energy storage device, the energy may be supplied to the medical device and/or energy storage device as at least one constant voltage, as maintained by constant voltage circuitry. In that case, the medical device and energy storage device may be provided with two different voltages, wherein at least one voltage is constant, maintained by the constant voltage circuitry.

Alternatively, when the energy received by the internal energy receiver is accumulated and stabilized in an energy stabilizing unit before energy is supplied to the medical device and/or energy storage device, the energy may be supplied to the medical device and/or energy storage device as at least one constant electric current, as maintained by a constant current circuitry. In that case, the medical device and energy storage device may be provided with two different electric currents wherein at least one electric current is constant, maintained by the constant current circuitry.

The energy may be initially wirelessly transferred according to a predetermined energy consumption plus a storage rate. In that case, the wireless transfer of energy may be turned off when a predetermined total amount of energy has been transferred. The energy received by the internal energy receiver may then also be accumulated and stabilized in an energy stabilizing unit before being consumed to operate the medical device and/or stored in the energy storage device until a predetermined total amount of energy has been consumed and/or stored.

Furthermore, the energy may be first wirelessly transferred with the predetermined energy rate, and then transferred based on the energy balance which can be determined by detecting the total amount of accumulated energy in the energy stabilizing unit. Alternatively, the energy balance can be determined by detecting a change in the current amount of accumulated energy in the energy stabilizing unit. In yet another alternative, the energy balance can be determined by detecting the direction and rate of change in the current amount of accumulated energy in the energy stabilizing unit.

The wireless transfer of energy may be controlled such that an energy reception rate in the internal energy receiver corresponds to the energy consumption and/or storage rate. In that case, the wireless transfer of energy may be turned off when a predetermined total amount of energy has been consumed.

The energy received by the internal energy receiver may be first accumulated and stabilized in an energy stabilizing unit, and then consumed or stored by the medical device until a predetermined total amount of energy has been consumed. In that case, the energy balance may be determined based on a detected total amount of accumulated energy in the energy stabilizing unit. Alternatively, the energy balance may be determined by detecting a change in the current amount of accumulated energy in the energy stabilizing unit. In yet another alternative, the energy balance may be determined by detecting the direction and rate of change in the current amount of accumulated energy in the energy stabilizing unit.

Suitable sensors may be used for measuring certain characteristics of the medical device and/or detecting the current condition of the patient, somehow reflecting the required amount of energy needed for proper operation of the medical device. Thus, electrical and/or physical parameters of the medical device and/or physical parameters of the patient may be determined, and the energy can then be transfer with a transfer rate which is determined based on the determined parameter values. Further, the wireless transfer of energy may be controlled such that the total amount of transferred energy is based on a determined value or values of said parameters.

The energy received by the internal energy receiver may be first accumulated and stabilized in an energy stabilizing unit, and then consumed until a predetermined total amount of energy has been consumed. The wireless transfer of energy may further be controlled such that an energy reception rate at the internal energy receiver corresponds to a predetermined energy consumption rate.

Further, electrical and/or physical parameters of the medical device and/or physical parameters of the patient may be determined, in order to determine the total amount of transferred energy based on the determined values of parameters. In that case, the energy received by the internal energy receiver may be first accumulated and stabilized in an energy stabilizing unit, and then consumed until a predetermined total amount of energy has been consumed.

The energy is stored in the energy storage device according to a predetermined storing rate. The wireless transfer of energy may then be turned off after a predetermined total amount of energy has been stored. The wireless transfer of energy can be further controlled such that an energy reception rate at the internal energy receiver corresponds to the predetermined storing rate.

The energy storage device of the medical device may comprise a first storage device and a second storage device, wherein the energy received by the internal energy receiver is first stored in the first storage device, and the energy is then supplied from the first storage device to the second storage device at a later stage.

When using the first and second storage devices in the energy storage device, the energy balance may be determined in different ways. Firstly, the energy balance may be determined by detecting the current amount of energy stored in the first storage device, and the wireless transfer of energy may then be controlled such that a storing rate in the second storage device corresponds to an energy reception rate in the internal energy receiver. Secondly, the energy balance may be determined based on a detected total amount of stored energy in the first storage device. Thirdly, the energy balance may be determined by detecting a change in the current amount of stored energy in the first storage device. Fourthly, the energy balance may be determined by detecting the direction and rate of change in the current amount of stored energy in the first storage device.

Stabilized energy may be first supplied from the first storage device to the second storage device as a constant electric current, as maintained by constant current circuitry, until a measured voltage over the second storage device reaches a predetermined maximum voltage, and thereafter supplied from the first storage device to the second storage energy storage device as a constant voltage, as maintained by constant voltage circuitry. In that case, the wireless transfer of energy may be turned off when a predetermined minimum rate of transferred energy has been reached.

The wireless transfer of energy may further be controlled such that the amount of energy received by the internal energy receiver corresponds to the amount of energy stored in the second storage device. In that case, the wireless transfer of energy may be controlled such that an energy reception rate at the internal energy receiver corresponds to an energy storing rate in the second storage device. The wireless transfer of energy may also be controlled such that a total amount of received energy at the internal energy receiver corresponds to a total amount of stored energy in the second storage device.

In the case where the wireless transfer of energy is turned off after a predetermined total amount of energy has been stored, electrical and/or physical parameters of the medical device and/or physical parameters of the patient may be determined during a first energy storing procedure, and the predetermined total amount of energy may be stored in a subsequent energy storing procedure based on the determined values of the parameters.

When values of electrical and/or physical parameters of the medical device and/or physical parameters of the patient are determined, the energy may be stored in the energy storage device with a storing rate which is determined based on the determined parameter values. In that case, a total amount of energy may be stored in the energy storage device, the total amount of energy being determined based on the parameters. The wireless transfer of energy may then be automatically turned off after the total amount of energy has been stored. The wireless transfer of energy may further be controlled such that an energy reception rate at the internal energy receiver corresponds to the storing rate.

When values of electrical and/or physical parameters of the medical device and/or physical parameters of the patient are determined, a total amount of energy may be stored in the energy storage device, the total amount of energy being determined based on the determined values of said parameters. The wireless energy transfer may then be controlled such that the total amount of received energy at the internal energy receiver corresponds to the total amount of stored energy. Further, the wireless transfer of energy may be automatically turned off after the total amount of energy has been stored.

When the energy used for the medical device is partly consumed and partly stored, the wireless transfer of energy may be controlled based on a predetermined energy consumption rate and a predetermined energy storing rate. In that case, the wireless transfer of energy may be turned off after a predetermined total amount of energy has been received for consumption and storage. The wireless energy transfer may also be turned off after a predetermined total amount of energy has been received for consumption and storage.

When values of electrical and/or physical parameters of the medical device and/or physical parameters of the patient are determined, the energy may be wirelessly transferred for consumption and storage according to a transfer rate per time unit which is determined based on the determined values of said parameters. The total amount of transferred energy may also be determined based on the values of said parameters.

When values of electrical and/or physical parameters of the medical device and/or physical parameters of the patient are determined, the energy may be supplied from the energy storage device to the medical device for consumption with a supply rate which is determined based on the determined values of said parameters. In that case, the total amount of energy supplied from the energy storage device to the medical device for consumption may be based on the determined values of said parameters.

When values of electrical and/or physical parameters of the medical device and/or physical parameters of the patient are determined, a total amount of energy may be supplied to the medical device for consumption from the energy storage device, where the total amount of supplied energy is determined based on the determined values of the parameters.

When the energy received by the internal energy receiver is accumulated and stabilized in an energy stabilizing unit, the energy balance may be determined based on an accumulation rate in the energy stabilizing unit, such that a storing rate in the energy storage device corresponds to an energy reception rate in the internal energy receiver.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or a monitored electric current related to the energy balance.

When using the first and second storage devices in the energy storage device, the second storage device may directly or indirectly supply energy to the medical device, wherein the change of the difference corresponds to a change of the amount of energy accumulated in the first storage unit. The energy balance may then be determined by detecting a change over time in the energy storing rate in the first storage device, the energy balance corresponding to the change. The change in the amount of stored energy may also be detected by determining over time the derivative of a measured electrical parameter indicating the amount of stored energy, the derivative corresponding to the change in the amount of stored energy. A rate of change of the electrical parameter may also be detected, the derivative being related to the change rate. The electrical parameter may be a measured voltage and/or a measured electric current related to the energy balance.

The first storage device may include at least one of: a capacitor and a semiconductor, and the second storage device includes at least one of: a rechargeable battery, an accumulator and a capacitor.

As mentioned above, the energy may be wirelessly transferred using electric induction from a primary coil in the external energy source to a secondary coil in the internal energy receiver. However, the energy may alternatively or additionally be transferred in other ways. For example, the energy may be transferred by sound or pressure variations, by radio waves or light. The wirelessly transferred energy may also be transferred as pulses or waves and/or by an electric field.

When the energy is wirelessly transferred from the external energy source to the internal energy receiver in pulses, the wireless transfer of energy may be controlled by adjusting the width of the pulses.

When the difference between the total amount of energy received by the internal energy receiver and the total amount of consumed energy is measured over time, directly or indirectly, the energy balance may be determined by detecting a change in the difference. In that case, the change in the amount of consumed energy may be detected by determining over time the derivative of a measured electrical parameter related to the amount of consumed energy, the derivative corresponding to the rate of the change in the amount of consumed energy, wherein the rate of change includes the direction and speed of the change. A rate of change of the electrical parameter may then be detected, the derivative being related to the detected change rate.

When using the first and second storage devices in the energy storage device, the first storage device may be adapted to be charged at a relatively higher energy charging rate as compared to the second storage device, thereby enabling a relatively faster charging. The first storage device may also be adapted to be charged at multiple individual charging occasions more frequently as compared to the second storage device, thereby providing relatively greater life-time in terms of charging occasions. The first storage device may comprise at least one capacitor. Normally, only the first storage may be charged and more often than needed for the second storage device.

When the second storage device needs to be charged, to reduce the time needed for charging, the first storage device is charged at multiple individual charging occasions, thereby leaving time in between the charging occasions for the first storage device to charge the second storage device at a relatively lower energy charging rate. When electrical parameters of the medical device are determined, the charging of the second storage device may be controlled based on the parameters. A constant current circuitry or stabilizing voltage circuitry may be used for storing energy in the second storage device.

Additional objects and advantages of the invention will be set forth in the description which follows, and in part will be obvious from the description, or may be learned by practice of the invention. The objects and advantages of the invention may be realized and obtained by means of the methods, processes, instrumentalities and combinations particularly pointed out in the appended claims.

BRIEF DESCRIPTION OF THE DRAWINGS

While the novel features of the invention are set forth with particularly in the appended claims, a complete understanding of the invention, both as to organization and content, and of the above and other features thereof may be gained from and the invention will be better appreciated from a consideration of the following detailed description of non-limiting embodiments presented hereinbelow with reference to the accompanying drawings, in which:

FIGS. 4-12 are diagrams illustrating measurements obtained for the circuit illustrated in FIG. 3.

DETAILED DESCRIPTION

A method and apparatus will now be described in which energy is wirelessly transferred from an external energy source located outside the body a mammal patient and is received by an internal energy receiver located inside the patient's body. The internal energy receiver is connected to an electrically operable medical device implanted in the patient's body, for directly or indirectly supplying received energy for powering the medical device. A feedback control signal is transmitted using a feedback communication system from an internal communication unit located inside the patient's body to an external communication unit located outside the patient's body, where the feedback control signal reflects a required amount of energy for operating the medical device.

An energy balance may be determined between the energy received by the internal energy receiver and the energy used for the medical device, and the wireless transfer of energy is then controlled based on the determined energy balance and in response to the feedback control signal. The energy balance may provides an accurate indication of the correct amount of energy needed, which is sufficient to operate the medical device properly, but without e.g. causing an undue temperature rise.

Figure 1:
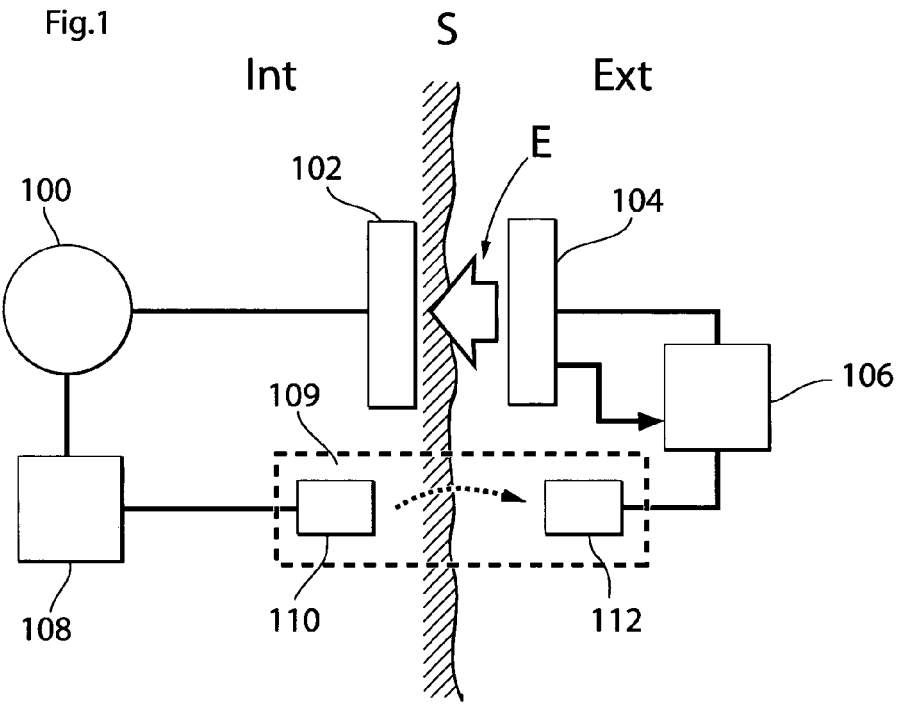
FIG. 1 is a schematic block diagram illustrating an arrangement for supplying an accurate amount of energy to an electrically operable medical device.

FIG. 1 is a schematic of apparatus for supplying an accurate amount of energy to an electrically operable medical device 100 implanted in a patient's body, the skin of which is indicated by a vertical line S separating the interior "Int" of the patient's body from the exterior "Ext". The medical device 100 is connected to an internal energy receiver 102, likewise located inside the patient, such as place just inside the skin S. Generally speaking, the energy receiver 102 may be placed in the abdomen, thorax, muscle fascia, e.g. in the abdominal wall, subcutaneously, or at any other suitable location. The energy receiver 102 is adapted to receive energy E wirelessly transferred from an external energy source 104 located outside the skin S in the vicinity of the energy receiver 102.

As is well-known in the art, the wireless energy E may generally be transferred by any suitable TET-device, e.g. a device using electric induction and including a primary coil, not shown, arranged in the energy source 104 and an adjacent secondary coil, not shown, arranged in the energy receiver 102. When an electric alternating current flows through the primary coil, an alternating voltage is induced in the secondary coil which, if connected to an electric load, makes an alternating electric current flow through the load and hence electric power or energy is transferred from the primary coil to secondary coil, this being the principle of an electric transformer. The electric load can e.g. be the medical device 100 and then the induced alternating electric current can be used to directly power the medical device. The electric load can alternatively include an energy storing device or accumulator, not shown, such as a battery or a capacitor, and then electric energy obtained from the induced voltage is stored in the energy storing device or accumulator. The stored energy can be used to power the medical device 100. However, the method and apparatus as described herein are generally not limited to any particular energy transfer technique, TET-devices or energy storing devices, and any kind of wireless transfer of energy may be used.

The amount of wirelessly transferred energy can be regulated by an external control unit 106 controlling the energy source 104 based on the determined energy balance and in response to the feedback control signal, as described above. In order to transfer the correct amount of energy, the energy balance and the required amount of energy may be determined by an internal control unit 108 connected to the medical device 100. The internal control unit 108 may be arranged to receive various measurements obtained by suitable sensors or the like, not shown, measuring e.g. certain characteristics of the medical device 100, somehow reflecting the required amount of energy required for a proper operation of the medical device 100. Moreover, the current condition of the patient may also be detected by suitable measuring devices or sensors, not shown, in order to provide values of parameters reflecting the patient's physical condition. Hence, such characteristics and/or parameters may be related to the current state of the medical device 100, such as its power consumption, operational mode and temperature, as well as the patient's condition reflected by e.g. body temperature, blood pressure, heart beat rate and breathing rate.

Furthermore, an energy storing device or accumulator, not shown here, may also be connected to the energy receiver 102 for accumulating received energy for later use by the medical device 100. Alternatively or additionally, characteristics of such an energy storing device, also reflecting the required amount of energy, may be measured as well. The energy storing device may be a battery, and the measured characteristics may be related to the current state of the battery, such as the voltage between the terminals thereof, the temperature, etc. In order to provide a sufficient voltage and electric current to the medical device 100, and also to avoid excessive heating, it is clearly understood that the battery should be charged optimally by receiving a correct amount of energy from the energy receiver 102, i.e. not too little or too much. The energy storing device may also be a capacitor having corresponding characteristics.

For example, battery characteristics may be measured on a regular basis to determine the current state of the battery, which then may be stored as state information in a suitable memory means, not shown, in the internal control unit 108. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 108 may be adapted to determine the energy balance and/or the currently required amount of energy—either energy per time unit or accumulated energy—based on measurements made by the above-mentioned sensors or measuring devices on the medical device 100, or the patient, or an energy storing device if used, or any combination thereof. The apparatus further comprises a feedback communication system 109 including an internal communication unit 110 and an external communication unit 112. The internal control unit 108 and the external communication unit 112 are connected to the internal communication unit and the external communication unit, respectively, in the communication system for transferring a feedback control signal reflecting the determined required amount of energy over the feedback communication system 109 to the external control unit 106. The amount of energy transferred from the energy source 104 may then be regulated in response to the received feedback control signal.

Alternatively, values of parameters obtained in sensor measurements, as described above, can be transferred to the external control unit 106. Then, the energy balance and/or the currently required amount of energy can be determined by the external control unit 106, thus integrating the above-described function of the internal control unit 108 in the external control unit 106. In that case, the internal control unit 108 can be omitted and the values determined in the sensor measurements are supplied directly to the internal communication unit 110 which transfers the determined values to the external communication device receiver 112 and therefrom to the external control unit 106. The energy balance and the currently required amount of energy can then be determined by the external control unit 106 based on those sensor measurements.

Hence, the method and apparatus as described herein employ feedback of information indicating the required energy, which is more efficient than previously suggested methods and devices because the feedback is based on the actual use of energy that is compared to the received energy, e.g. with respect to the amount of energy, the energy difference, or the energy receiving rate as compared to the energy rate used by the medical device 100. The medical device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the medical device 100.

The feedback communication system 109 can use capacitive signal transmission, the internal communication unit 110 including a first capacitor plate, not shown, and the external communication unit including a second capacitor plate, not shown, the two capacitor plates forming together with the region located between the plates an electric capacitor.

To conclude, the energy supply apparatus illustrated in FIG. 1 may operate basically in the following manner. The energy balance may be first determined by the internal control unit 108. A feedback control signal reflecting the required amount of energy is also created by the internal control unit 108 and the feedback control signal is transmitted the external control unit 108 over the feedback communication system 109. Alternatively, the energy balance can be determined by the external control unit 106 instead, depending on the implementation, as mentioned above. In that case, the feedback control signal may carry values measured by one or more sensors. The amount of energy transferred from the energy source 104 can then be regulated by the external control unit 106 in response to the received feedback control signal, e.g. based on the determined energy balance. This process may be repeated intermittently at certain intervals during ongoing energy transfer, or may be executed on a more or less continuous basis during the wireless energy transfer.

The amount of transferred energy can generally be regulated by adjusting parameters in the energy source 104, such as voltage, current, amplitude, wave frequency and pulse characteristics depending on the type of physical device used for the energy transfer.

Figure 2:
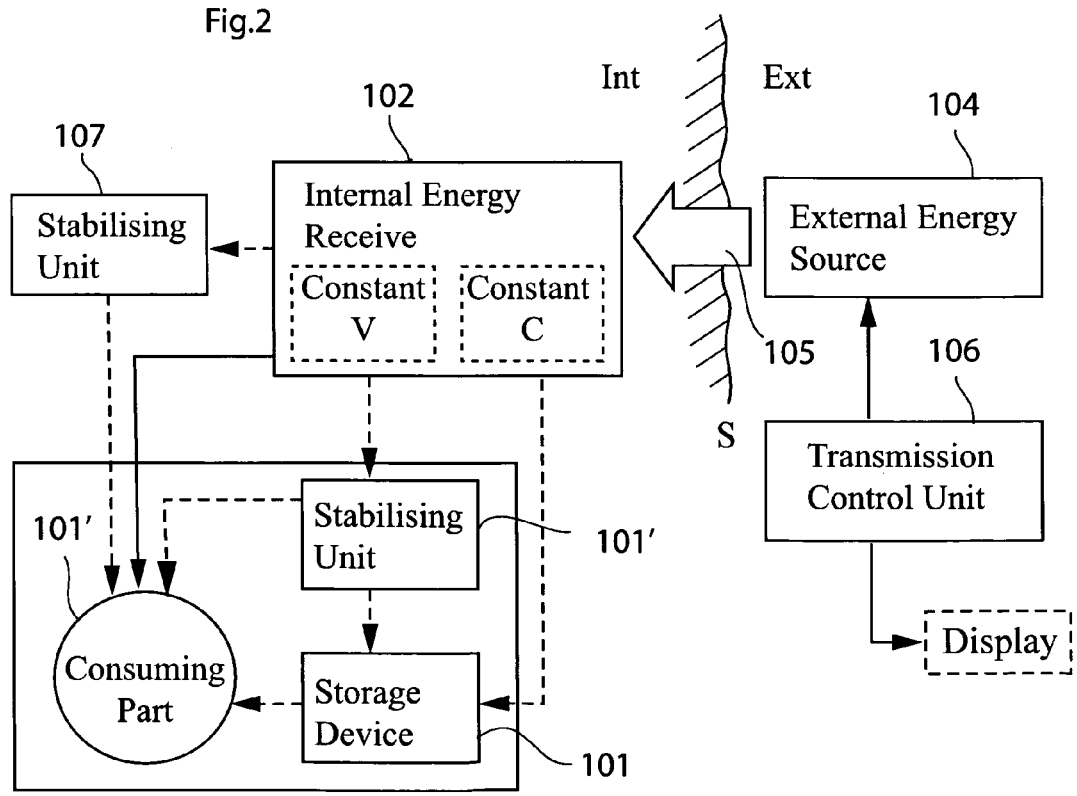
FIG. 2 is a more detailed block diagram of an apparatus for controlling wireless transfer of energy to an electrically operable medical device implanted in a patient's body.

FIG. 2 is a schematic illustrating embodiments of different ways of supplying wirelessly transferred energy to the medical device 100. The internal energy receiver 102 receives energy, see the arrow 105, that is wirelessly transferred from the external energy source 104 which is controlled by an external control unit 106. The internal energy receiver 102 may comprise a constant voltage circuit 103 for supplying electric energy at a constant voltage to the medical device 100. The internal energy receiver 102 may further comprise a constant current circuit 103' for supplying energy at a constant electric current to the medical device 100.

The medical device 100 comprises an energy consuming part 100' which may be a motor, pump, restriction device, or any other medical appliance that requires energy for its operation. The medical device 100 may further comprise an energy storage device 101 for storing energy supplied from the internal energy receiver 102. Thus, the supplied energy may be directly consumed by the energy consuming part 100' or stored by the energy storage device 101, or the supplied energy may be partly consumed and partly stored. The medical device 100 may further comprise an energy stabilizing unit 101' for stabilizing the energy supplied from the internal energy receiver 102. Thus, the energy may be supplied in a fluctuating manner such that it may be necessary to stabilize the supply of energy before being consumed or stored.

The energy supplied from the internal energy receiver 102 may further be accumulated and/or stabilized by a separate energy stabilizing unit 107 located outside the medical device 100, before being consumed by and/or stored in the medical device. Alternatively, the energy stabilizing unit 107 may be integrated in the internal energy receiver 102. In either case, the energy stabilizing unit 107 may comprise a constant voltage circuit and/or a constant current circuit, not shown.

It should be noted that FIGS. 1 and 2 illustrate some possible but non-limiting implementation options regarding how the various shown functional components and elements can be arranged and connected to each other. However, the skilled person will readily appreciate that many variations and modifications can be made.

As mentioned above, the energy may be transferred by electric induction from a primary coil in the external energy source 104 to a secondary coil in the internal energy receiver 102.

A change in the energy balance may be detected to control the wireless transfer of energy based on the detected energy balance change. A difference may also be detected between energy developed in the internal energy receiver and energy used for the medical device to control the wireless transfer of energy based on the detected energy difference.

When controlling the energy transfer, the amount of wirelessly transferred energy per time unit may be decreased if the detected energy balance change implies that the energy balance is increasing, or vice versa. The decrease/increase of the wireless energy transfer per time unit may further correspond to a detected change rate.

The amount of wirelessly transferred energy per time unit may further be decreased if the detected energy difference implies that the received energy per time unit is greater than the used energy per time unit, or vice versa. The decrease/increase of energy transferred per time unit may then correspond to the magnitude of the detected energy difference.

As mentioned above, the wirelessly transferred energy may be consumed to operate the medical device 100, and/or stored in at least one energy storage device 101 of the medical device.

In one alternative, substantially all energy used for the medical device 100 is directly consumed, e.g. by the consuming part 100', to operate the medical device. In that case, the energy may be consumed after having been stabilized in at least one energy stabilizing unit 101' of the medical device.

In another alternative, substantially all energy used for the medical device 100 is first stored in the at least one energy storage device 101. In yet another alternative, the energy used for the medical device is partly directly consumed to operate the medical device and partly stored in the at least one energy storage device.

The energy received by the internal energy receiver 102 may be stabilized by being provided to a capacitor, not shown, before the energy is supplied directly or indirectly to the medical device 100.

The difference between the total amount of energy received by the internal energy receiver 102 and the total amount of consumed and/or stored energy may be directly or indirectly measured over time, and the energy balance can then be determined based on a detected change in the difference between total amount.

The energy received by the internal energy receiver 102 may further be accumulated and stabilized in an energy stabilizing unit such as 107, before the energy is supplied to the medical device 100. In that case, the energy balance may be determined based on a detected change followed over time in the amount of consumed and/or stored energy. Further, the change in the amount of consumed and/or stored energy may be detected by determining over time the derivative of a measured electrical parameter related to the amount of consumed and/or stored energy, where the derivative at a first given moment corresponds to the rate of the change at the first given moment, the rate of change including the direction and the velocity of the change. The derivative may further be determined based on a detected rate of change of the measured electrical parameter.

The energy received by the internal energy receiver 102 may be supplied to the medical device 100 as at least one constant voltage, wherein the constant voltage is created by constant voltage circuitry 103. In that case, the energy may be supplied as at least two different voltages, including the at least one constant voltage.

The energy received by the internal energy receiver 102 may also be supplied to the medical device 100 as at least one constant electric current, wherein the constant electric current is created by constant current circuitry 103'. In that case, the energy may be supplied as at least two different electric currents including the at least one constant electric current.

The energy balance may also be determined based on a detected difference between the total amount of energy received by the internal energy receiver 102 and the total amount of consumed and/or stored energy, the detected difference being related to the integral over time of at least one measured electrical parameter related to the energy balance. In that case, values of the electrical parameter may be plotted over time as a graph in a parameter-time diagram, and the integral can be determined from the size of the area beneath the plotted graph. The integral of the electrical parameter may relate to the energy balance as an accumulated difference between the total amount of energy received by the internal energy receiver 102 and the total amount of consumed and/or stored energy.

The energy storage device 101 in the medical device may include at least one of: a rechargeable battery, an accumulator or a capacitor. The energy stabilizing unit 101', 107 may include at least one of: an accumulator, a capacitor or a semiconductor adapted to stabilize the received energy.

When the energy received by the internal energy receiver 102 is accumulated and stabilized in an energy stabilizing unit 107 or 101' before energy is supplied to the medical device 100, in particular its consuming part 100', and/or to the energy storage device 101, the energy may be supplied to the medical device and/or the energy storage device as at least one constant voltage, as maintained by constant voltage circuitry 103. In that case, the medical device and energy storage device may be provided with at least two different voltages, wherein at least one voltage is constant, maintained by the constant voltage circuitry.

Alternatively, when the energy received by the internal energy receiver 102 is accumulated and stabilized in an energy stabilizing unit 107 or 101' before energy is supplied to the medical device 100, in particular to its consuming part 100', and/or to the energy storage device 101, the energy may be supplied to the medical device and/or the energy storage device as at least one constant electric current, as maintained by constant current circuitry 103'. In that case, the medical device and energy storage device may be provided with at least two different electric currents wherein at least one electric current is constant, maintained by the constant current circuitry.

The wirelessly transferred energy may be initially transferred according to a predetermined energy consumption plus storage rate. In that case, the wireless energy transfer may be turned off after a predetermined total amount of energy has been transferred. The energy received by the internal energy receiver 102 may then also be accumulated and stabilized in an energy stabilizing unit such as 107 or 101' before being consumed to operate the medical device 100, in particular the consuming part 100' thereof, and/or stored in the energy storage device such as 101 until a predetermined total amount of energy has been consumed and/or stored.

Furthermore, the wirelessly transferred energy may be first transferred with the predetermined energy rate, and then transferred with an energy rate based on the energy balance which can be determined by detecting the total amount of accumulated energy in the energy stabilizing unit 107, 101' (or 101). Alternatively, the energy balance can be determined by detecting a change in the current amount of accumulated energy in the energy stabilizing unit. In yet another alternative, the energy balance can be determined by detecting the direction and rate of change in the current amount of accumulated energy in the energy stabilizing unit.

The wireless transfer of energy may be controlled such that an energy reception rate in the internal energy receiver corresponds to the energy consumption and/or storage rate. In that case, the wireless transfer of energy may be turned off after a predetermined total amount of energy has been consumed.

The energy received by the internal energy receiver 102 may be first accumulated and stabilized in an energy stabilizing unit 107, 101', and then consumed or stored by the medical device 100 until a predetermined total amount of energy has been consumed. In that case, the energy balance may be determined based on a detected total amount of accumulated energy in the energy stabilizing unit. Alternatively, the energy balance may be determined by detecting a change in the current amount of accumulated energy in the energy stabilizing unit. In yet another alternative, the energy balance may be determined by detecting the direction and rate of change in the current amount of accumulated energy in the energy stabilizing unit.

As mentioned above when discussing FIG. 1, one or more suitable sensors may be used for measuring certain characteristics of the medical device and/or detecting the current physical condition of the patient, somehow reflecting the required amount of energy needed for a proper operation of the medical device 100. Thus, values of electrical and/or physical parameters of the medical device and/or physical parameters of the patient's body may be determined, and the energy can then be transferred with a transfer rate which is determined based on the measured values of the parameters. Furthermore, the wireless energy transfer may be controlled such that the total amount of transferred energy is based on the value or values of said one more parameters.

The energy received by the internal energy receiver 102 may be first accumulated and stabilized in an energy stabilizing unit 107, 101' (or 101), and then consumed until a predetermined total amount of energy has been consumed. The wireless energy transfer may further be controlled such that an energy reception rate at the internal energy receiver corresponds to a predetermined energy consumption rate.

Furthermore, values of one or more electrical and/or physical parameters of the medical device 100 and/or physical parameters of the patient may be determined, in order to determine the total amount of transferred energy based on the measured values of the parameters. In that case, the energy received by the internal energy receiver 102 may be first accumulated and stabilized in an energy stabilizing unit 107, 101' (and/or 101), and then consumed until a predetermined total amount of energy has been consumed.

The energy is stored in the energy storage device 101 according to a predetermined storing rate. The wireless energy transfer may then be turned off after a predetermined total amount of energy has been stored. The wireless energy transfer can be further controlled such that an energy reception rate at the internal energy receiver 102 corresponds to the predetermined storing rate.

The energy storage device 101 of the medical device 100 may comprise a first storage device and a second storage device, not shown, wherein the energy received by the internal energy receiver 102 is first stored in the first storage device, and the energy is then supplied from the first storage device to the second storage device at a later stage.

When using such first and second storage devices in the energy storage device 101, the energy balance may be determined in different ways. Firstly, the energy balance may be determined by detecting the current amount of energy stored in the first storage device, and the wireless energy transfer may then be controlled such that a storing rate in the second storage device corresponds to an energy reception rate in the internal energy receiver 102. Secondly, the energy balance may be determined based on a detected total amount of stored energy in the first storage device. Thirdly, the energy balance may be determined by detecting a change in the current amount of stored energy in the first storage device. Fourthly, the energy balance may be determined by detecting the direction and rate of change in the current amount of stored energy in the first storage device.

Stabilized energy may be first supplied from the first storage device to the second storage device as a constant electrical current, as maintained by constant current circuitry, not shown, until a measured voltage over the second storage device reaches a predetermined maximum voltage, and thereafter supplied from the first storage device to the second storage energy storage device as a constant voltage, as maintained by constant voltage circuitry, not shown. In that case, the wireless energy transfer may be turned off after a predetermined minimum rate of transferred energy has been reached.

The wireless energy transfer may further be controlled such that the amount of energy received by the internal energy receiver 102 corresponds to the amount of energy stored in the second storage device. In that case, the wireless energy transfer may be controlled such that an energy reception rate at the internal energy receiver corresponds to an energy storing rate in the second storage device. The wireless energy transfer may also be controlled such that a total amount of received energy at the internal energy receiver 102 corresponds to a total amount of stored energy in the second storage device.

In the case where the wireless energy transfer is turned off after a predetermined total amount of energy has been stored, one ore more electrical and/or physical parameters of the medical device 100 and/or one ore more physical parameters of the patient may be determined during a first energy storing procedure, and the predetermined total amount of energy may be stored in a subsequent energy storing procedure based on the determined value or values of the parameter or parameters.

In the case where values of one or more electrical and/or physical parameters of the medical device 100 and/or of one or more physical parameters of the patient are determined, the energy may be stored in the energy storage device 101 with a storing rate which is determined based on the determined value or values of the parameters. In that case, a total amount of energy may be stored in the energy storage device, the total amount of energy being determined based on the value or values of the one or more parameters. The wireless energy transfer may then be automatically turned off after the total amount of energy has been stored. The wireless energy transfer may further be controlled such that an energy reception rate at the internal energy receiver 102 corresponds to the storing rate.

In the case where values of one or more electrical and/or physical parameters of the medical device 100 and/or of one or more physical parameters of the patient are determined, a total amount of energy may be stored in the energy storage device 101, the total amount of energy being determined based on the value or values of said parameters. The wireless energy transfer may then be controlled such that the total amount of received energy at the internal energy receiver 102 corresponds to the total amount of stored energy. Furthermore, the wireless energy transfer may be automatically turned off after the total amount of energy has been stored.

When the energy used for the medical device 100 is partly consumed and partly stored, the wireless energy transfer may be controlled based on a predetermined energy consumption rate and a predetermined energy storing rate. In that case, the wireless energy transfer may be turned off after a predetermined total amount of energy has been received for consumption and storage. The wireless energy transfer may also be turned off after a predetermined total amount of energy has been received for consumption and storage.

When one or more electrical and/or physical parameters of the medical device 100 and/or one or more physical parameters of the patient are determined, the energy may be transferred for consumption and storage according to a transfer rate per time unit which is determined based on the determined value or values of said parameters. The total amount of transferred energy may also be determined based on the determined value or values of said parameters.

When one or more electrical and/or physical parameters of the medical device 100 and/or one or more physical parameters of the patient are determined, the energy may be supplied from the energy storage device 101 to the medical device 100, in particular the consuming part 100' thereof, for consumption with a supply rate which is determined based on the determined value or values of said parameters. In that case, the total amount of energy supplied from the energy storage device to the medical device for consumption may be based on the determined value or values said parameters.

When one ore more electrical and/or physical parameters of the medical device 100 and/or one or more physical parameters of the patient are determined, a total amount of energy may be supplied to the medical device for consumption from the energy storage device 101, where the total amount of supplied energy is determined based on the determined value or values of said parameters.

When the energy received by the internal energy receiver 102 is accumulated and stabilized in an energy stabilizing unit 107, 101' (and/or 101), the energy balance may be determined based on an accumulation rate in the energy stabilizing unit, such that a storing rate in the energy storage device corresponds to an energy reception rate in the internal energy receiver.

When a difference is detected between the total amount of energy received by the internal energy receiver 102 and the total amount of consumed and/or stored energy, and the detected difference is related to the integral over time of at least one measured electrical parameter related to said energy balance, the integral may be determined for a monitored voltage and/or monitored electric current related to the energy balance.

When the derivative is determined over time of a measured electrical parameter related to the amount of consumed and/ or stored energy, the derivative may be determined for a monitored voltage and/or a monitored electric current related to the energy balance.

When using first and second storage devices being part of the energy storage device 101, the second storage device may directly or indirectly supply energy to the medical device 100, wherein the change of the difference corresponds to a change of the amount of energy accumulated in the first storage unit. The energy balance may then be determined by detecting a change over time in the energy storing rate in the first storage device, the energy balance corresponding to the change. The change in the amount of stored energy may also be detected by determining over time the derivative of a measured electrical parameter indicating the amount of stored energy, the derivative corresponding to the change in the amount of stored energy. A rate of change of the electrical parameter may also be detected, the derivative being related to the change rate. The electrical parameter may be a measured voltage and/or a measured electric current related to the energy balance.

The first storage device may include at least one of: a capacitor and a semiconductor, not shown, and the second storage device includes at least one of: a rechargeable battery, an accumulator and a capacitor, not shown.

As mentioned above, the energy may be transferred inductively from a primary coil in the external energy source to a secondary coil in the internal energy receiver. However, the wireless energy may also be transferred non-inductively. For example, the wireless energy may be transferred by sound or pressure variations, radio waves or light. The wirelessly transferred energy may also be transferred as pulses or waves and/or by means of an electric field.

When the wirelessly transferred energy is transferred from the external energy source 104 to the internal energy receiver 102 in pulses or bursts of pulses or of an oscillation or wave, such as in amplitude modulation, the wireless energy transfer may be controlled by adjusting the width of the pulses or bursts.

When the difference between the total amount of energy received by the internal energy receiver 102 and the total amount of consumed energy is measured over time, directly or indirectly, the energy balance may be determined by detecting a change in the difference. In that case, the change in the amount of consumed energy may be detected by determining over time the derivative of a measured electrical parameter related to the amount of consumed energy, the derivative corresponding to the rate of the change in the amount of consumed energy, wherein the rate of change includes the direction and speed of the change. A rate of change of the electrical parameter may then be detected, the derivative being related to the detected change rate.

When using first and second storage devices being part of the energy storage device 101, the first storage device may be adapted to be charged at a relatively higher energy charging rate as compared to the second storage device, thereby enabling a relatively faster charging. The first storage device may also be adapted to be charged at multiple individual charging occasions more frequently as compared to the second storage device, thereby providing relatively greater lifetime in terms of charging occasions. The first storage device may comprise at least one capacitor, not shown. Normally, only the first storage may be charged more often than what is required for the second storage device.

When the second storage device needs to be charged, to reduce the time needed for charging, the first storage device is charged at multiple individual charging occasions, thereby leaving time in between the charging occasions for the first storage device to charge the second storage device at a relatively lower energy charging rate. When one or more electrical parameters of the medical device 100 are determined, the charging of the second storage device may be controlled based on the determined value or values of said parameters. Constant current or stabilizing voltage circuitry, not shown, may be used for storing energy in the second storage device.

Figure 3:
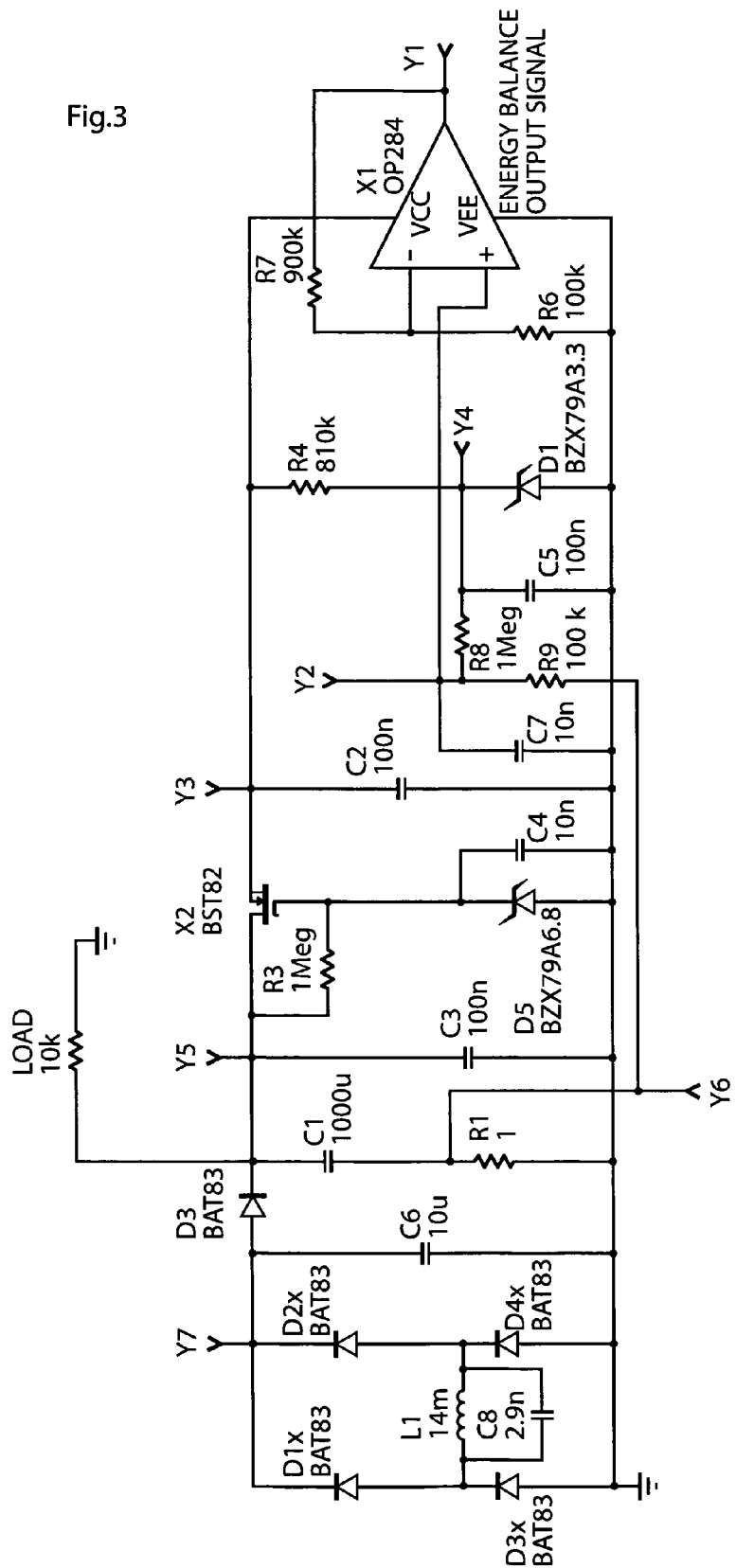
FIG. 3 is a schematic circuit diagram illustrating a design of an apparatus for controlling wireless transfer energy.

FIG. 3 is a circuit diagram of one possible design of a device providing a signal for controlling wireless energy transfer, arranged e.g. in the internal control device 108, or generally of an energy balance control or measuring circuit. The energy balance measuring circuit has an output signal which is centered on 2.5 V and the deviation of which from 2.5 V is proportional to the energy imbalance. Thus, a signal level of 2.5 V means that there an energy balance exists, if the signal level drops below 2.5V energy is drawn from the power source in the implant and if the voltage level rises above 2.5 V energy is charged to the storage device 101. The signal output from the circuit is typically feed to an A/D converter, not shown, to be converted into a digital format. The digital information can then be sent to the external control device 106 allowing it to adjust the level of the wirelessly transferred power. Another possibility is to have a completely analog system that uses comparators comparing the energy balance level to appropriately set maximum and minimum thresholds and that sends information to the external control device if the balance drifts out of the window defined by the thresholds.

The circuit implementation of FIG. 3 is designed for apparatus in which power is transferred to the implant or medical device 100 from outside the patient's body using inductive energy transfer. An inductive energy transfer system typically uses an external coil and an internal coil. The internal receiving coil is drawn as the inductor L1 in the circuit diagram of FIG. 3.

The general concept of determining and using an energy balance and the way in which feedback information is transmitted to the external control device 106 can of course be implemented in numerous different ways. The schematic of FIG. 3 and the method of evaluating and transmitting such information described above should only be regarded as examples of how the control system and parts thereof can be implemented.

The symbols Y1, Y2, Y3, etc. in FIG. 3 symbolize test points within the circuit. References to the test points are found on the graphs in diagrams that will be described hereinafter. The components in the diagram and their respective values are values that may work in this particular implementation which of course is only one of an infinite number of possible designs.

Energy is transferred to the internal coil L1, e.g. at a frequency of 25 kHz. The energy balance output signal is present at test point Y1.

Figure 4:
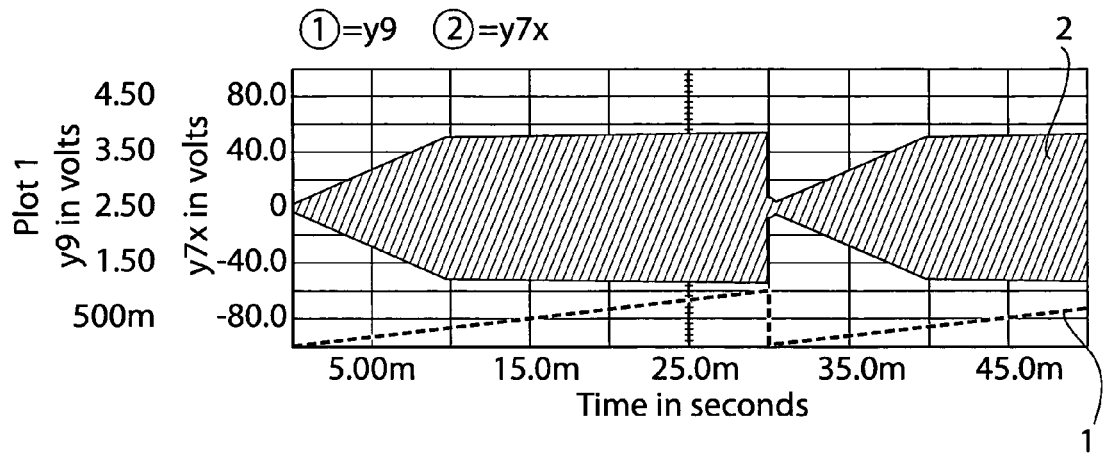

The diagram of FIG. 4 shows the voltage Y7$x$ over the internal coil L1 and the power Y9 transferred to the coil. The power graph Y9 is normalized and varies between 0 and 1, where 1 denotes maximum power and 0 that no power is transferred from the external coil. The power graph Y9 is an amplitude modulation signal modulating the alternating current supplied to the external, primary coil. In the diagram it can be seen that the Y7$x$ voltage over the internal coil L1 increases as the transferred power increases. When the Y7$x$ voltage reaches the level where actual charging of the storage device 101 in the implanted medical device 100 commences the Y7$x$ level increases at a much slower rate as the input power is increased because of the load that the storage device imparts on the internal coil.

Figure 5:
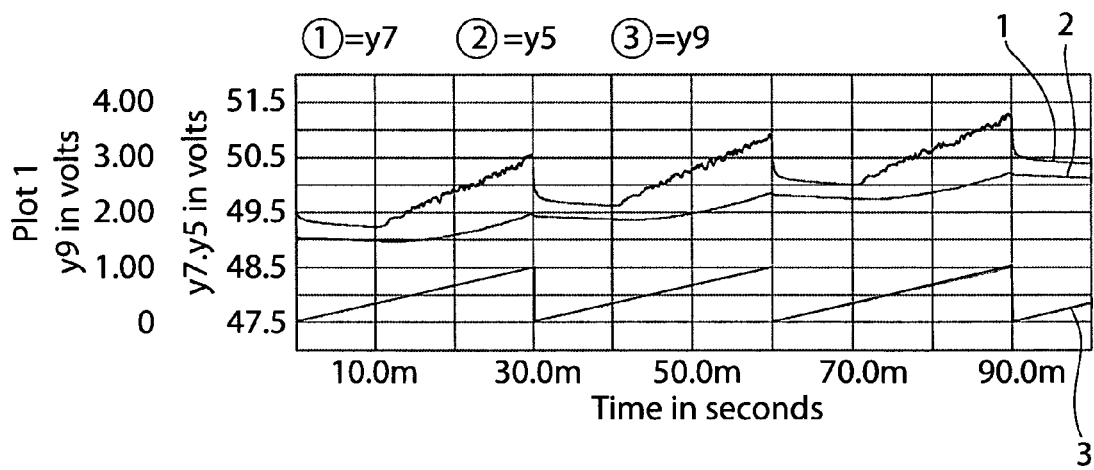

The internal coil L1 is connected in a rectifying bridge including with four Schottky diodes D1x-D4x. The voltage output from the bridge Y7 is shown in the diagram of FIG. 5. The capacitor C6 absorbs the high frequency charging currents from the bridge and together with the Schottky diode D3 prevents the 25 kHz energy transmission frequency from entering the rest of the circuit. This is beneficial since the energy balance of the system is measured as the voltage across the resistor R1, which without the C6-D3 combination would contain a high level of 25 kHz alternating current. The storage device in the medical device 100 is represented by the capacitor C1. The capacitor C3 is a high frequency decoupling capacitor. The resistor LOAD is a fictive load representing the storage device 101 in the implant. The voltage Y5 over the storage device source is also shown in the diagram of FIG. 5 together with the power graph Y9.

Figure 6:
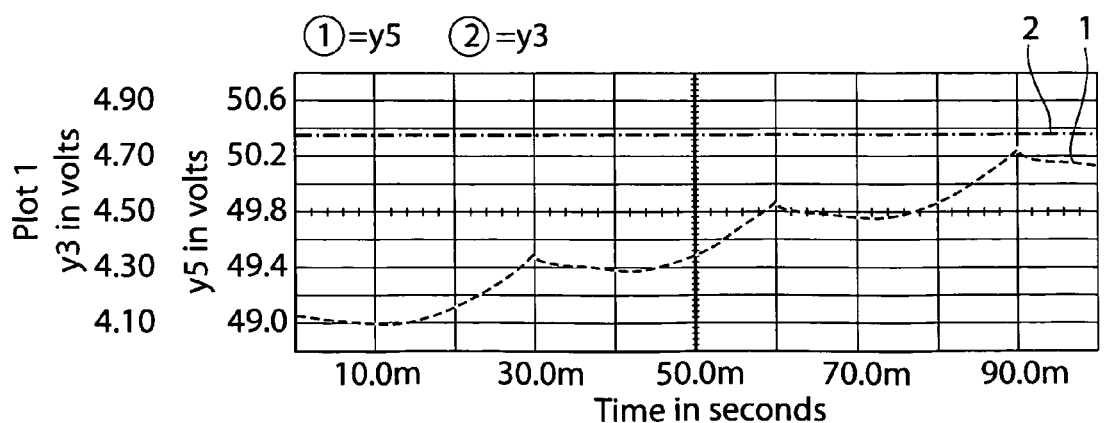

The voltage Y3 in the diagram of FIG. 6 is a stabilized voltage of about 4.8 V used to power the operational amplifier X1. The Y3 voltage is stabilized by a fairly standard linear voltage regulator consisting of the MOSFET X2, the Zener diode D5, the capacitor C4 and the resistor R3. The capacitor C2 is a high frequency decoupling capacitor. In the diagram of FIG. 6 the voltage input to the regulator is seen at Y5 and the output voltage is Y3.

Figure 7:
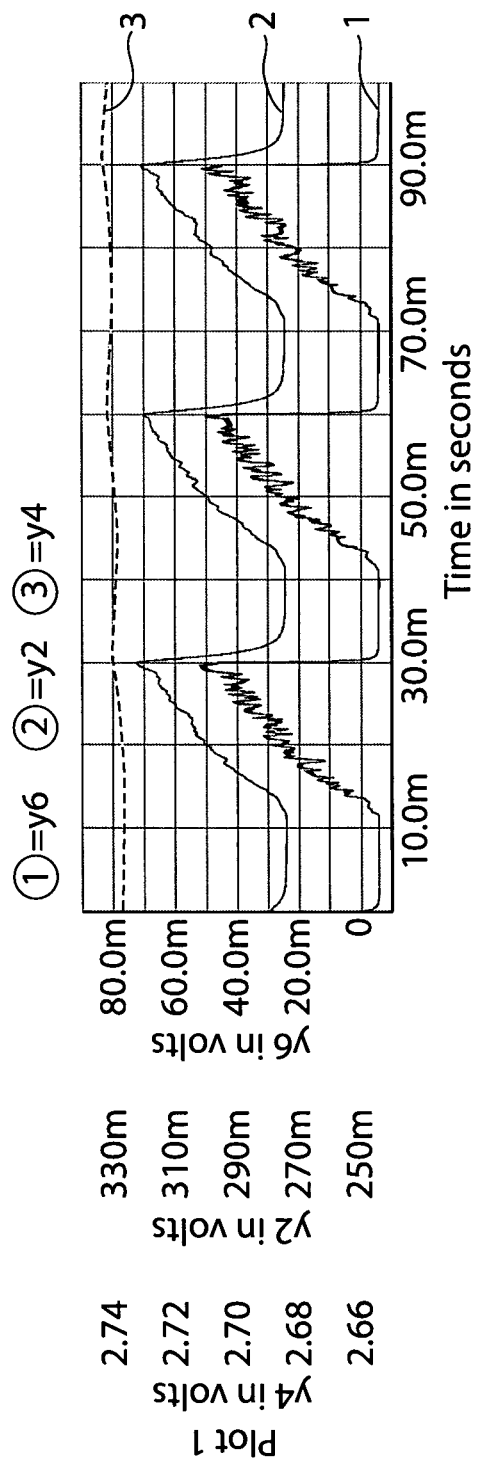

The operational amplifier X1 is used to amplify the energy balance signal together with the resistors R6 and R7 that set the gain of the amplifier circuit to e.g. 10 times. The signals input to the circuit are shown in the diagram of FIG. 7. Y4 is fixed at a more or less constant level of approximately 2.74 V by the Zener diode D1. The voltage Y4 is shunted and high frequency filtered by the capacitor C5. A part of the DC voltage at Y4 is coupled into the Y2 voltage by the resistor R8 in order to center the output voltage Y1 at 2.5 V when energy is balanced. The voltage Y2 is basically the same voltage as the voltage Y6 over the resistor R1, only slightly high frequency filtered by the resistor R9 and the capacitor C7 and shifted in DC level by the electric current flowing through the resistor R8. To compare Y6 and Y2 the diagram of FIG. 7 can be considered.

The energy balance output signal Y1 of the circuit, as seen in the diagram of FIG. 8, also closely correspond to the voltage Y6. The voltage Y1 is an amplified, e.g. 10 times, and DC shifted to be centered around 2.5 V instead of 0 V version of the voltage Y6. The higher signal level at Y1 and the DC center point around 2.5 V are much easier to interface to for the circuits connected to the energy balance output signal.

The diagram of FIG. 9 shows the relationship between the energy balance signal Y1 and the actual voltage over the storage device 101 (or stabilizing unit 101', 107) for the implant 100. The energy balance signal is the derivative of the voltage level Y5 over the power source. When the energy balance signal Y1 is negative relative to 2.5 V the voltage level Y5 is lowered and when the energy balance signal is positive relative to 2.5 V the voltage Y5 increases. The more negative or positive relative to 2.5 V the energy balance signal Y1 is the more rapidly the voltage Y5 over the storage device increases or decreases.

The diagram of FIG. 10 of another circuit condition perhaps even more clearly shows how the energy balance signal corresponds to the derivative of the voltage Y5 over the storage device. The traces show a situation in which the power fed into the storage device is held at a constant level and the load is varied to absorb between 5 mA and 30 mA in four discrete steps. During the first 25 ms the load is set to absorb 30 mA, the following 25 ms it is set to 5 mA, then followed by the same 30 mA and 5 mA sequence. When the voltage Y5 over the storage device decreases at a constant level due to the load absorbing 30 mA the derivative level is at a constant level below 2.5 V and when the voltage Y5 increases the derivative voltage is positive at a constant level.

Figure 11A:
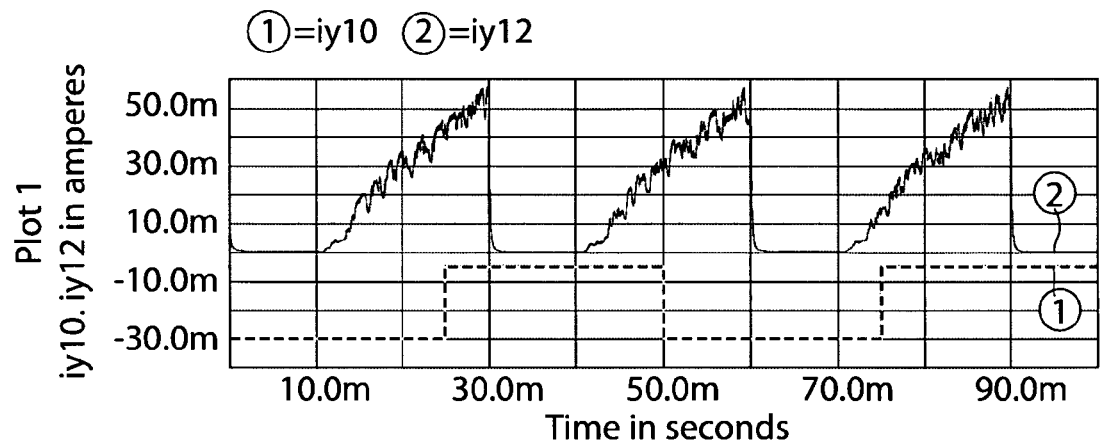
Figure 11B:
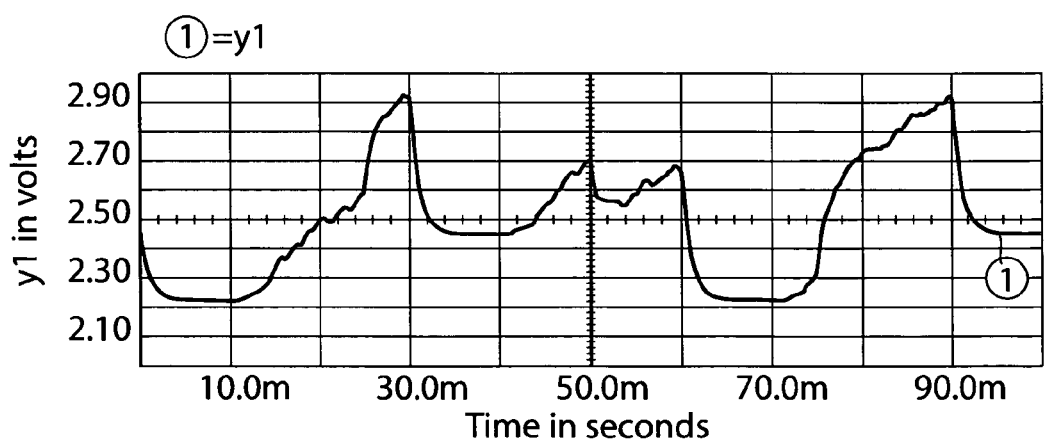

The two diagrams of FIGS. 11a, 11b show the relationship between the energy balance signal Y1 and the energy imbalance in the circuit in a complex situation where both the load is varied and the amount of power fed to the implant is varied. The two traces in the diagram of FIG. 11a show the charging electric current supplied to the storage device source and the load current. The charging electric current is represented by the trace IY12 and the load current is represented by the trace IY10. The diagram of FIG. 11b shows the voltage Y1 generated by the altering currents shown in the diagram of FIG. 11a. When the amount of stored energy in the storage device is changed due to the energy imbalance the derivative signal Y1 rapidly responds to the imbalance as shown in the diagram.

Figure 12:
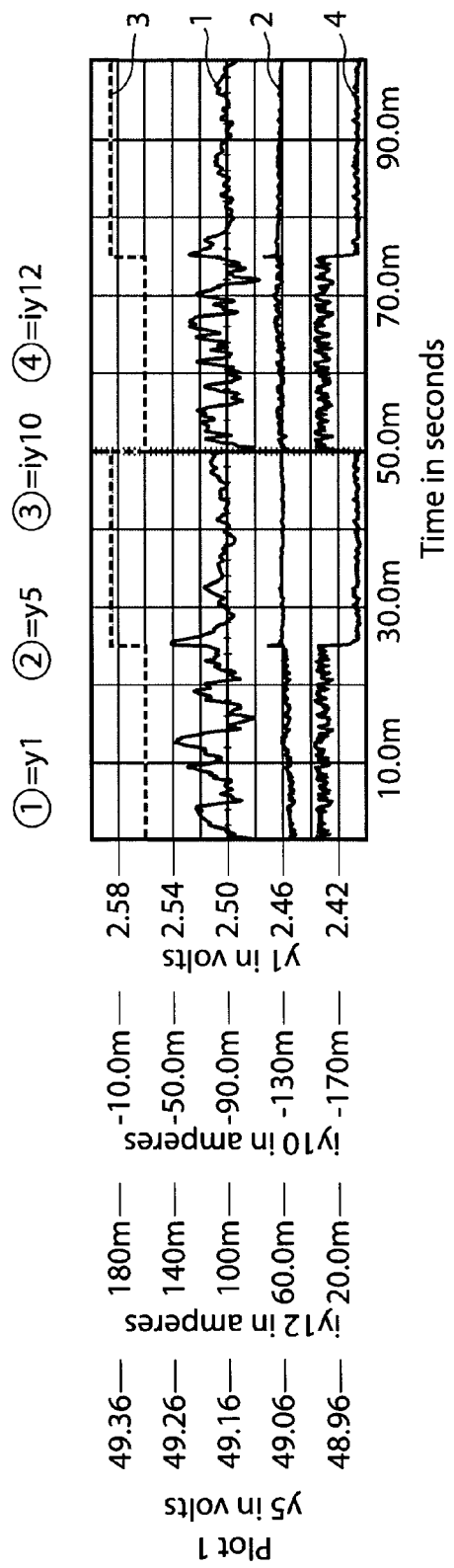

In a system where the energy balance signal is used as a feedback signal to an external control device 106, allowing it to regulate the transferred power according to the energy imbalance, it is possible to maintain an optimal energy balance and to keep the efficiency at a maximum. The diagram of FIG. 12 shows the charging electric current fed to the storage device and the load current, the charging current represented by the trace IY12 and the load current by the trace IY10, as well as the voltage level Y5 over the storage device and the energy balance signal Y1 in such a system. It can clearly be seen that this system rapidly responds to any load current changes by increasing the charging electric current. Only a small spike in the energy balance signal can be seen right at the edges where the load is rapidly changed due to the finite bandwidth of the feedback loop. Apart from those small spikes the energy is kept in perfect balance.

Figure 13:
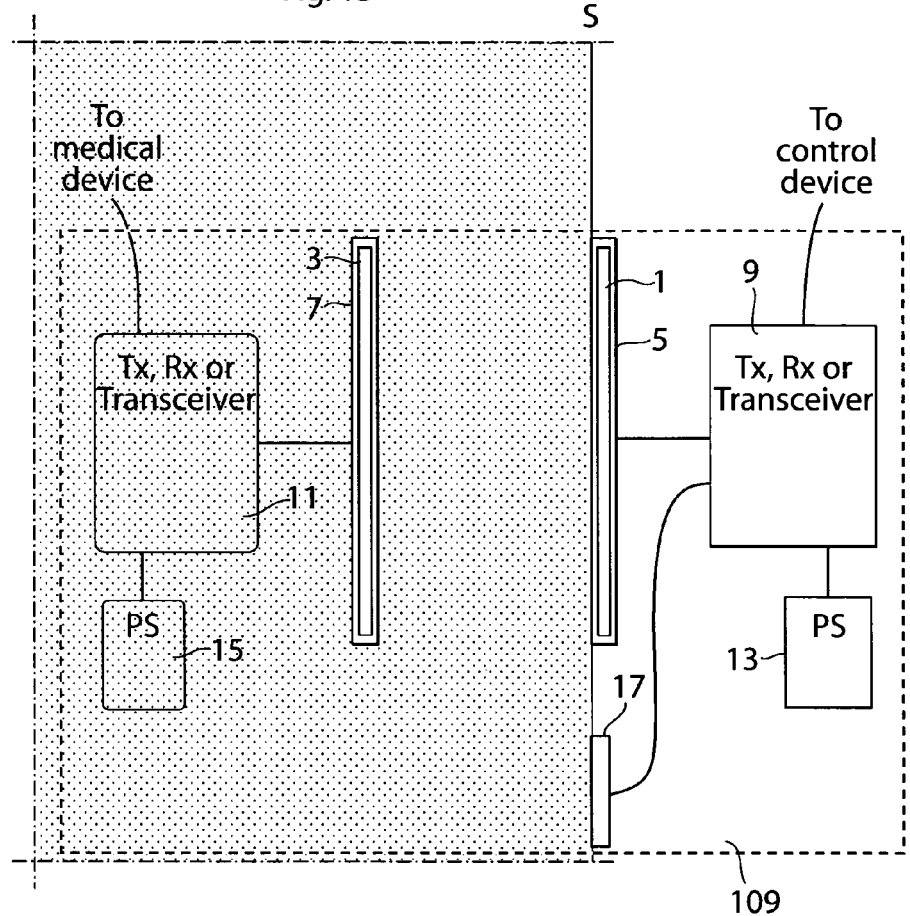
FIG. 13 is a schematic of a feedback communication system.

In the case where the feedback communication system 109 uses capacitive signal transmission, it may be designed as schematically illustrated in FIG. 13. The feedback communication system includes an electric capacitor formed by two capacitor plates 1, 3 and intermediate regions of material, in particular a region of the patient's body. The first capacitor plate 1 is located outside the body of the person in which the device is implanted. The plate can be applied to the skin of the person's body or be placed in a close vicinity thereof. The second capacitor plate 3 is located inside the person's body and is thus also an implant. Since the body tissues are electrically conducting, the capacitor plates 1, 3 must be electrically insulated in order to form the intended capacitor. Hence, each of the capacitor plates is embedded in an electrical insulator 5, 7, the insulator e.g. forming a thin layer totally surrounding the respective plate that is made from an electrically conducting material, e.g. a well conducting material such as copper.

The capacitor plates 1, 3 are electrically conducted to driver circuits 9, 11, respectively, which basically can include transmitter, receiver or transceiver circuits. The driver circuits 11 for the internal capacitor plate 3 are thus also implanted and are electrically connected to the implanted device 100 or the internal control device 108 therefor, not shown in this figure. The external driver circuits 9 are connected to the external control device 106, not shown in this figure. The driver circuits are powered by power supplies 13, 15, the internal one also being implanted, where these power supplies can be common to devices inside or outside the skin S, respectively. The driver circuits may require a common electrical ground potential which can make the transfer of information more secure. It can be provided by e.g. having the housing of the internal driver circuits 11 be electrically conducting, and thus in electrical connection with the body tissues. The external driver circuits 9 can be electrically connected to an electrically conducting plate or electrode 17 that is electrically attached to the skin of the person's body in the same way as electrodes e.g. for cardiography.

The capacitor formed by the capacitor plates 1, 3 is part of an electric circuit connection between the driver circuits 9, 11 and electric signals can be transmitted over this circuit connection. By selecting the dimensions of the plates and their location in relation to each other the capacitor can be given a capacitance suited for the signal transfer. Hence, the plates can be made to have as large a surface area as is possible for an implant, e.g. in the range of 2-8 cm$^2$, and be configured in a suitable way. Of course, they may be rectangular or square plates but they may also e.g. have an elongated round shape or a circular shape. In particular, the internal capacitor plate 3 can be given a suitable shape, making it suitable to be implanted. Thus, it may e.g. have perforations or through-holes, not shown, allowing it to be securely attached in body tissues.

Figure 14:
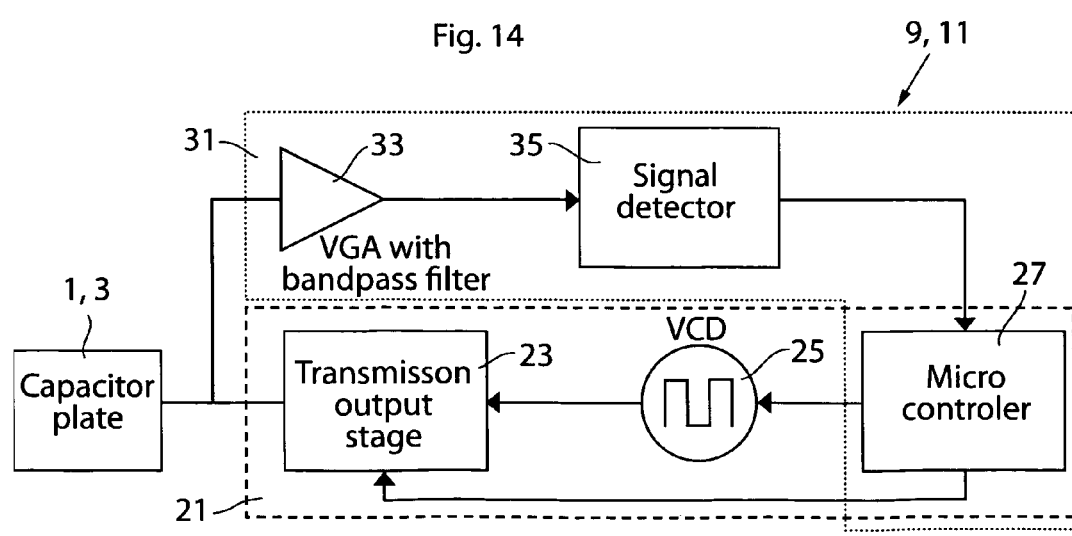
FIG. 14 is an overview circuit diagram of driver circuits in the feedback communication system of FIG. 13.

The driver circuits can be designed as is schematically illustrated in FIG. 14. The capacitor plate 1, 3 is thus connected to a transmission stage 21 that includes a transmission output stage 23, receiving an input signal a wave or alternating electric signal from an oscillator circuit 25, e.g. a voltage controlled oscillator (VCO) as illustrated, the oscillator circuit and the transmission output stage both being controlled by a microcontroller 27 such as for commanding a special wave form and for modulating it, respectively. The capacitor plate is also connected to a receiving stage 31, that includes an amplifier 33 also working as a bandpass filter. The amplifier provides its output signal to a signal detector 35 which delivers the detected information signal to the microcontroller 27. The driver circuits for the external and internal capacitor plates can include either of the transmission and receiving stages 21, 31 or both. The microcontroller can be the type PIC16F818 and it thus controls the transmission and receiving stage. For the receive mode, the microcontroller converts the signal level received from the signal detector 35, then using an ADC such the on-chip 8-bit ADC built into the PIC16F818.

Figure 15:
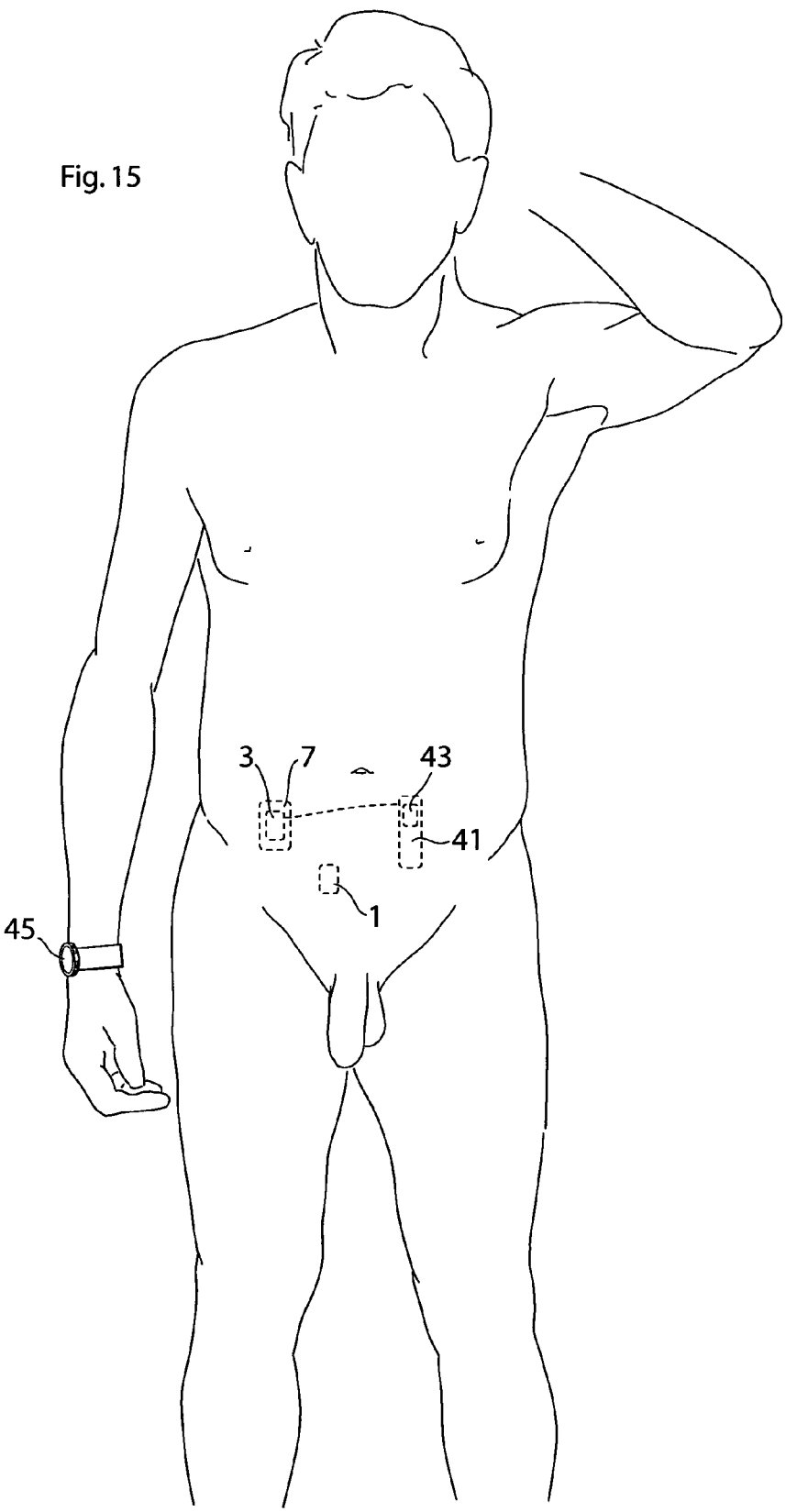
FIG. 15 is a schematic illustrating two ways of locating the feedback communication system of FIG. 13.

The system can be arranged on a person's body such as illustrated in FIG. 15. The capacitor plates 1, 3 can e.g. be arranged at the person's waist region. The internal capacitor plate 3 is seen to be surrounded by the electrical insulator 7, this for instance comprising two electrically insulated sheets between the electrically conducting plate is placed, the sheets being welded to each other at their margin region to provide a hermetic enclosure. In particular, the internal capacitor plate can be integrated with its driver circuits and power supply in one enclosure, the driver circuits connected to an implanted device 41 having its own power supply 43, e.g. an electrochemical cell. Alternatively, the driver circuits can be integrated with control circuits provided for the implanted device and then the power supply 43 also supplies power to the driver circuits.

In a special embodiment, the external capacitor plate 1 and its driver circuits 9 and power supply 13 can be integrated in a wristwatch 45. The internal capacitor plate 3, not seen in FIG. 15 for this case, may be located directly under the person's skin region.

Figure 16A:
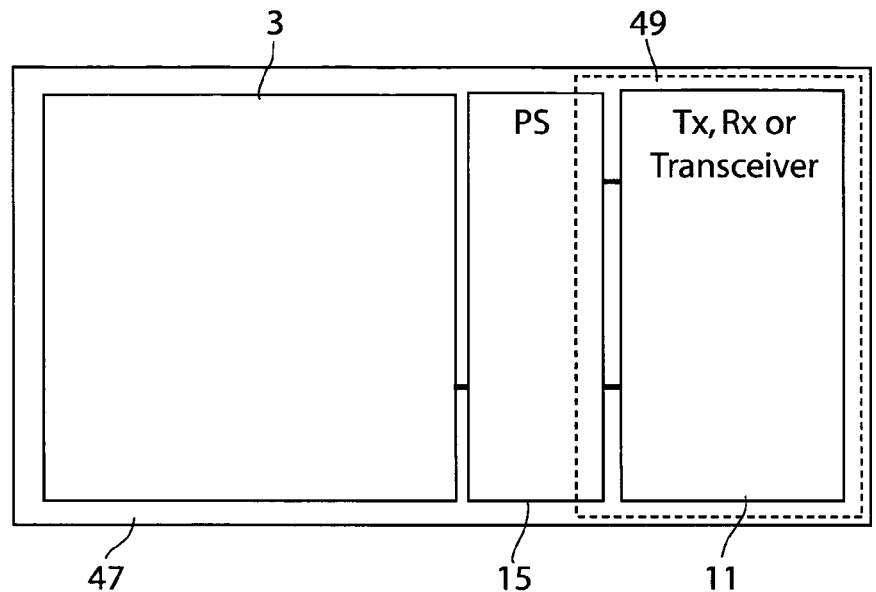
FIG. 16a is a front view of internal components of the feedback communication system of FIG. 13 in a common housing.

In FIG. 13 the driver circuits 11, the power supply 15 and the internal capacitor plate 3 are seen to be separate units, only connected by electrical cables. They can also be integrated as one single unit, placed at the sides of each other inside a common enclosure or housing 47, see FIG. 16*a*, which can be made from an electrically insulating material, forming the necessary electrically insulation of the capacitor plate.

The communication channel or path having a capacitive coupling as described above should have a constant impedance which is as small as possible in order to ensure that the communication signals are appropriately transferred. However, the capacitance of the capacitor used having one capacitor plate implanted in a patient's body is not constant due to the facts that the plates can move in relation to each other and that body functions in the tissues located between the capacitor plates can change. The frequency used for the communication is substantially constant if e.g. a carrier signal which is modulated is used or pulses of a definite frequency is used. Also, the frequency has to be as large as possible to make the impedance small.

Figure 16B:
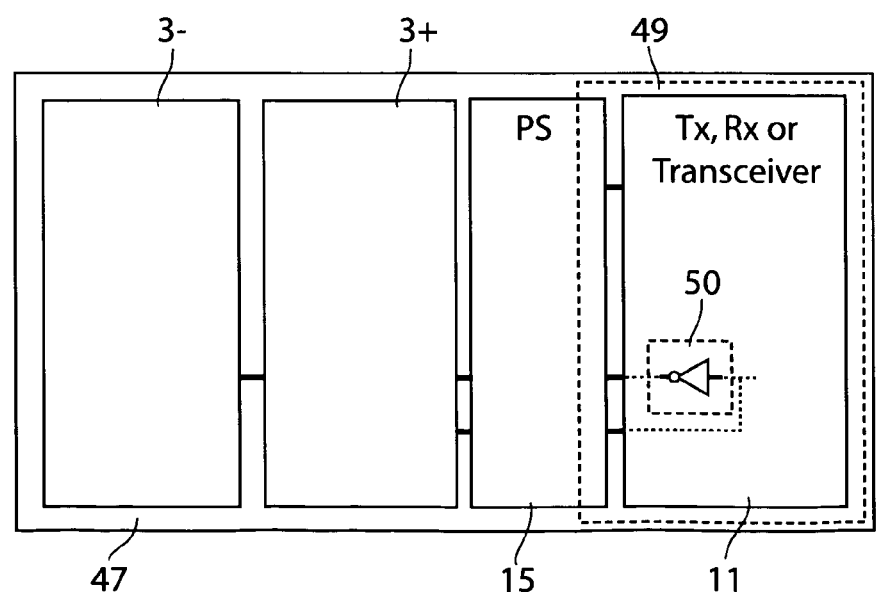
FIG. 16b is a front view similar to FIG. 16a of an alternative embodiment.

In order to improve the total capacitive coupling between the capacitor plates 1, 3 they can be divided to each include a first plate and a second plate, see FIG. 16*b*. For transmitting a signal through the capacitor, the two plates on the sending side can be then provided with signals which are the inverse of each other. Thus, e.g. the first plate can be provided with the direct signal and be denoted 3+ and the second plate can be provided with the inverted signal and then be denoted 3−. The inversion of signals can be easily achieved by arranging an inverter circuit such as that indicated at 50. For receiving an inverter circuit, not shown, having the opposite direction can be used. The external capacitor plate 1 must be configured in a similar and corresponding way, having one portion, not shown, for the direct signal and one portion, not shown, for the inverted signal.

Figure 16C:
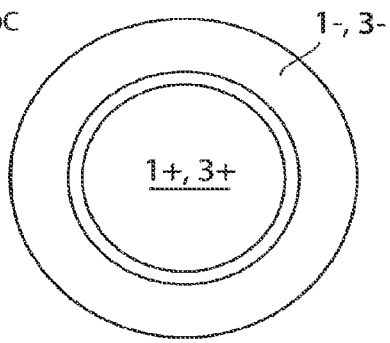
FIG. 16c is a picture of a possible design of dual capacitor plates.

The dual capacitor plates used in this case can for ease of positioning be configured as concentric circular fields, as seen in FIG. 16*c*, at least one of which is annular. One capacitor portion 1+, 3+ can, e.g., be a central circular field that is surrounded by an annular circular field 1−, 3−.

Various ways of communicating signals over the communication path involving a capacitive coupling can be conceived, considering the above mentioned conditions of the signal transmission, and some possible methods will now be described.

In the simplest case, the signals used in the communication between the external and internal devices can e.g. be electric pulses, e.g. substantially rectangular pulses. However, since the communication of information in most case must be made with a high degree of security, a suitable coding of the information could be used. Hence, e.g. Manchester coding can be used.

Manchester encoding is a special case of binary phase shift keying where each bit of data is signified by at least one transition. The encoding is therefore self-clocking which makes accurate synchronization of the data stream possible. For example, a "1" can be represented by a transition from a high to a low level and a "0" can be represented by a transition from a low to a high electrical level. This means that in the derivative of the electrical signal, there are variations so that a "1" can be seen as a negative pulse and a "0" as a positive pulse. In the electrical signal there are also transitions between the two levels that do not represent any information but are necessary in order that the transitions representing information can be arranged in the electrical, such extra transitions thus inserted when sending two equal consecutive bits of information.

Figure 17A:
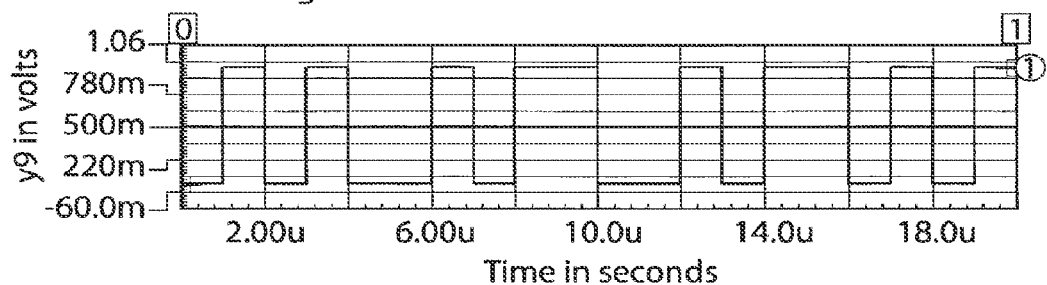
FIG. 17a is a diagram of pulses generated by a microcontroller according to a Manchester scheme.
Figure 18:
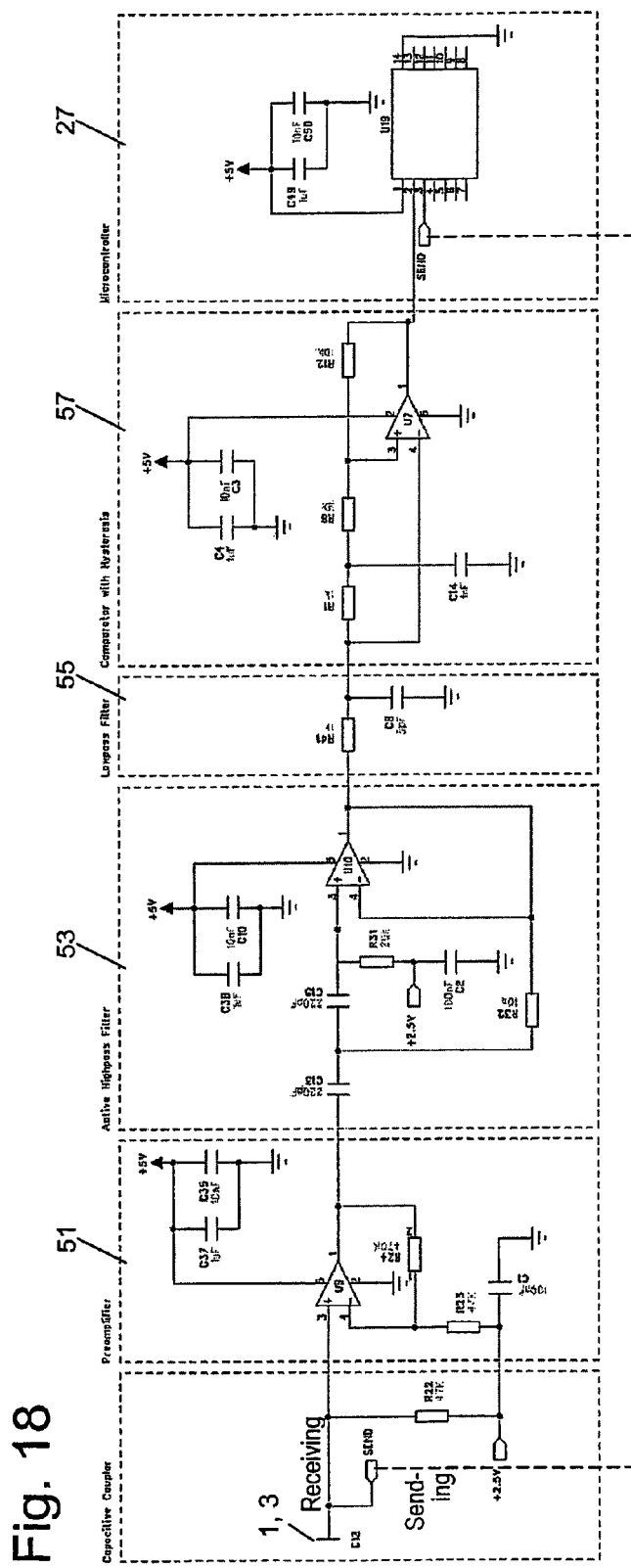
FIG. 18 is a circuit diagram of a transceiver that uses Manchester coded and is included in the feedback communication system of FIG. 13.

For these case of simple pulse transmission, the transmitter output stage 23 and the oscillator 25 illustrated in the circuit diagram of FIG. 14 may not be required since the pulses can be generated directly in the microprocessor 27 and provided to the respective capacitor plate 1, 3. A typical Manchester encoded signal generated by a microcontroller is illustrated in the diagram of FIG. 17a. FIG. 18 is a circuit diagram of driver circuits 9, 11 comprising a transceiver that can be used in this case.

For receiving, the transmitted signal is picked up by the capacitor plate 1, 3. The DC level of the signal is by the resistor R22 pulled to 2.5V which is equal to VCC/2. The received signal is provided to a preamplifier stage 51 including an amplifier U9 before it is passed to filter stages. The amplifier has a high input impedance and a low bias current. The signal is then provided to a highpass filter stage 53 that is configured as a second order active high pass filter including an amplifier U10 as its active element. This filter stage removes low frequency interfering signals and noise. Then, the signal is passed to a lowpass filter stage 55 being a passive filter of RC-type, comprising a resistor R41 and a capacitor C8 to remove high frequency noise.

Figure 17B:
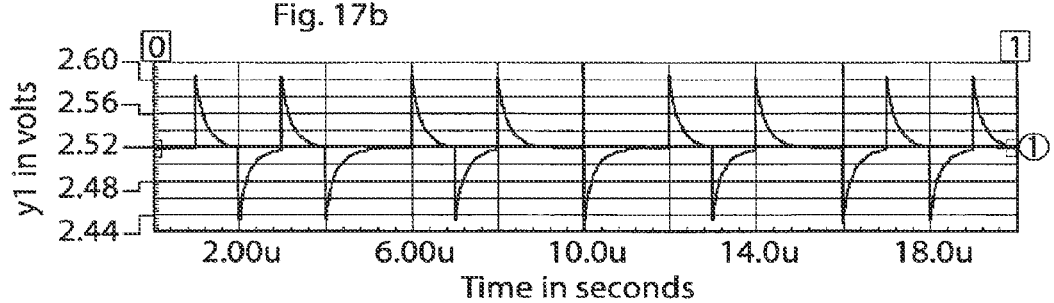
FIG. 17b is a diagram of signals detected in a first stage.
Figure 17C:
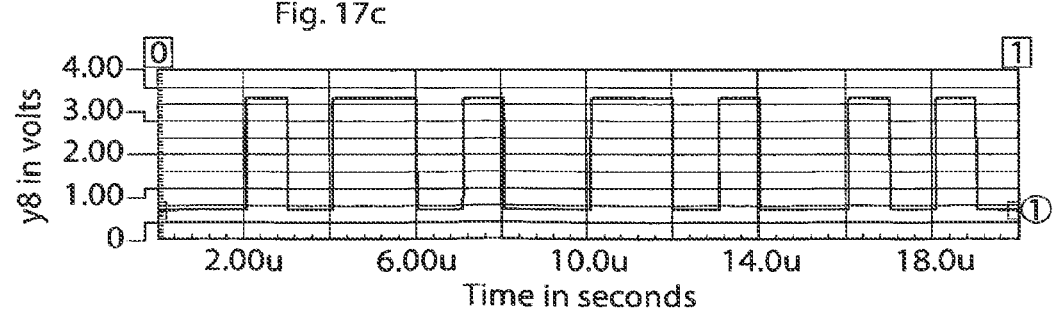
FIG. 17c is a diagram of signals detected by a comparator.

The signal is then provided to a signal detector stage that here is designed as a comparator 57 stage having hysteresis. Thus, the received and filtered signal is fed to the inverting input of a comparator U7. The same signal is also first even more low pass filtered in a passive RC-filter including R41 and C14 and then fed to the non-inverting input of the comparator via a resistor R6. The resistor R6 and the feedback resistor R12 form the hysteresis feedback. The comparator U7 has hysteresis in order to output a square wave in Manchester code even if the signal drops down below the DC level. An example of a received and filter signal can be seen in FIG. 17b and the output from the comparator U7 in FIG. 17c.

The microcontroller U19 is used to decode the received Manchester stream into useful data. This is achieved by measuring the time between rising and falling edges. When a reception is initialized, the microcontroller receives a preamble consisting of the repeated pattern "10101010". Since the only transitions that occur in that pattern are the bit transitions the preamble can be used to synchronize the data, i.e. to form a clock signal. When synchronization has been accomplished, the microcontroller can begin to translate the Manchester stream into useful data.

Another method is to use amplitude modulation to transfer data. For instance, a carrier frequency can be on/off-modulated to output bursts of the electrical signal.

Figure 19:
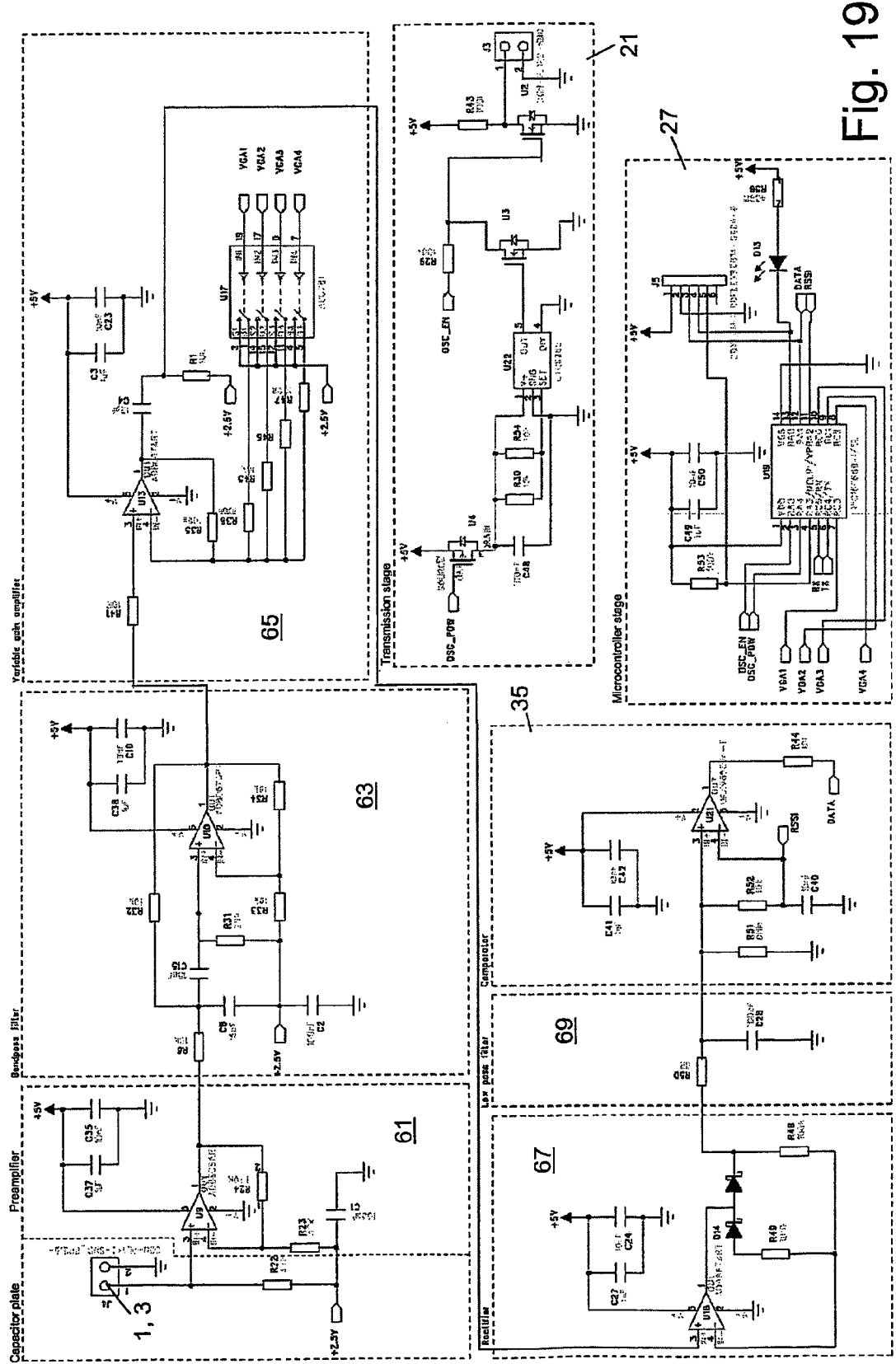
FIG. 19 is similar to FIG. 18 but of a transceiver that uses amplitude modulation.

For this method driver circuits like those illustrated in FIG. 19 may for instance be used. The transmission stage 21 has a signal generator U22, that can be enabled by a signal "OSC_POW" from the microcontroller U19 in the microcontroller stage, the signal opening a transistor U4. The signal generator U22 outputs a oscillatory signal having a frequency of about 1.4 MHz that is set by the resistors R30 and R54. The output from the signal generator U22 is fed to the gate of another transistor U3. Another signal "OSC_EN" from the microcontroller is used to modulate the amplitude of the signal by being provided the gate of a transistor U2. The transistor U2 and resistor R43 are provided to make it possible to transmit a voltage higher than 5V.

For receiving information, the transmitted signal is picked up by the capacitor plate connected to J4. The DC level of the received signal is by the resistor 22 pulled to 2.5V which is equal to VCC/2. The received is provided to a preamplifier stage 61 including an amplifier U9 having a high input impedance and a low bias current. The amplified signal is passed to a bandpass filter 63. The bandpass filter is a second order active band pass filter including an amplifier U10 as its active element. The filtered signal is provided to a variable gain amplifier 65 including a non-inverting amplifier U13. A resistor connects the inverting input of the non-inverting amplifier to a reference voltage that can be chosen by setting an analog switch U17. The gain of the variable gain amplifier 65 can therefore be set by the microcontroller 27 by control signals "VGA1-4". After having passed the variable gain amplifier, the signal is half-wave rectified in a rectifier stage 67 including an the amplifier U18 having two diodes D14 connected in its feedback loop. The rectified signal is by a passive low pass RC-filter 69 including a resistor R50 and a capacitor C28 to output a rectangular wave. The rectangular wave is high when the amplitude of the received signal is high or on and it is low when the amplitude is off or zero. Finally, the wanted signal is detected in a signal detector or comparator stage 35 by being provided to the non-inverting input of a comparator U21. The signal is also simultaneously low pass filtered by the RC-filter arranged by the resistor R52 and the capacitor C40 to provide an averaged signal to the inverting input. The signal "DATA" output from the comparator U21 is fed to the microcontroller 27 to decode the received data.

For the data reception to work properly in this case it may be important that the transmitted signal is balanced in the meaning that it is on and off for the same amount of time. The data can for that reason, also in this case, be encoded using Manchester code as described above.

A development of the simple amplitude modulation method using a carried that is switched on and off is the method called frequency shift keying (FSK). This modulation scheme represents a digital '0' with a first frequency and a '1' with a second, different frequency where these frequencies can be selected to be as large as possible. If possible, also rectangular waves can be used instead of sine waves to get a better transmission through the capacitive link.

In demodulating, in this case a received frequency is transformed into a '0' or '1'. This can be done using a phase locked loop (PLL), in particular a digital phase locked loop (DPLL). Such a digital demodulating circuit comprises a pfd or phase detector, a loop filter, a VCO counter and a decider. The phase detector looks on the incoming signal and compares it to the generated signal in the VCO counter. If any of the signals goes high before the other, this information is sent to the loop filter. The loop filter gets the information about which signal goes high first and translates this to a control signal for the VCO counter. This signal is the preset for the counter inside VCO counter. The VCO counter is a counter that always counts down and has a load and preset inputs. These inputs are controlled by the loop filter. The decider is a unit or circuit which creates the data signal. This is done by looking at the preset signals and, depending on the value, choosing between a '0' and a '1'.

While specific embodiments of the invention have been illustrated and described herein, it is realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention. Numerous other embodiments may be envisaged without departing from the spirit and scope of the invention.

The invention claimed is:

1. Apparatus configured to supply energy to a medical implant, comprising:
   a receiver adapted to be implanted in a mammal patient's body, an external energizer adapted to wirelessly transfer energy to the receiver, and a feedback communication system configured to send feedback information from the receiver to the external energizer, the feedback information being related to the transfer of energy to the receiver, wherein the feedback communication system is adapted to communicate the feed back information using the patient's body as an electrical capacitive conducting signal line, two capacitive capacitor plates, one capacitor plate being adapted configured to contact the inside of the mammal patient's body, the other capacitor plate is configured to be the outside of the mammal patient's body, each capacitor plate being divided so as to comprise a first dividing plate or portion and a second dividing plate or portion in order to improve the total capacitive coupling between the two capacitor plates, wherein the two dividing plates or portions on a sending side are adapted to be provided with signals which are the inverse of each other, when transmitting a signal through the capacitor, such that the first dividing plate or portion is configured to be provided with a direct signal and the second dividing plate is configured to be provided with an inverted signal, and an inverter circuit for the inversion of signals communicating with the outside capacitor plate, one dividing plate or portion of the external capacitor plate being provided with the direct signal and the other dividing plate or portion being provided with the inverted signal.

2. The apparatus according to claim 1, wherein
a first energy balance between the amount of energy received in the receiver and the energy used by the medical implant is followed over time, and
the feedback communication system sends information related to the first energy balance.

3. The apparatus according to claim 1, wherein
a second energy balance between the amount of energy received in the receiver and the amount of wireless energy transmitted from the external energizer is followed over time,
information related to the received amount of energy is sent via the feedback communication system from the patient's body, and
the external energizer is adapted to be moved along the patients skin to reach a position where the second energy balance is optimized for a maximum energy transfer to the receiver.

4. The apparatus according to claim 1, wherein the communication path between the receiver and the energizer via the patient's body has a relatively high electrical resistance to reduce the electrical current flowing in the communication path through the patient's body.

5. The apparatus according to claim 4, wherein the communication path between the receiver and the external energizer is established using a capacitive coupling, so that the feedback communication system communicates using the capacitive coupling.

6. The apparatus according to claim 5, wherein
the feedback communication system has an external communication unit that is connected to the external energizer and comprises a part of a capacitive energy storage, and
the feedback information, transmitted using the capacitive coupling, is represented by electrical currents injected into or drawn from the capacitive energy storage.

7. The apparatus according to claim 5, wherein
the feedback communication system has an internal communication unit that is connected to the receiver energizer and comprises a part of a capacitive energy storage, and
the feedback information, transmitted using the capacitive coupling, is represented by electrical currents injected into or drawn from the capacitive energy storage.

8. The apparatus according to claim 5, wherein
the feedback communication system has an external communication unit that is connected to the external energizer and comprises a first part of a capacitive energy storage, and
the feedback communication system has an internal communication unit that is connected to the receiver energizer and comprises a second part of a capacitive energy storage, and
the feedback information, transmitted using the capacitive coupling, is represented by electrical currents injected into or drawn from the capacitive energy storage.

9. The apparatus according to claim 6, wherein the feedback information is in a digital form and is represented by variations of the derivative of the voltage over the capacitive energy storage.

10. The apparatus according to claim 5, wherein
at least one of the external communication unit and the internal communication unit comprises a comparator configured to compare at least two different received frequencies,
at least the other of the external communication unit or the internal communication unit configured to send out at least two different frequencies, and
a communication path is established in digital form between the external communication unit and the internal communication unit using the different frequencies and said comparator placed at the other end of the communication path.

11. The apparatus according to claim 1, wherein said receiver comprises an internal coil.

12. The apparatus according to claim 1, wherein the energizer comprises an external coil.

13. The apparatus according to claim 12, wherein the second energy balance is related to the coupling factor between the internal and external coil.

14. The apparatus according to claim 12, further comprising a display unit for showing the energy balance during a movement of the energizer.

15. A method of supplying energy to a medical implant using an apparatus according to claim 1, the method comprising the steps of:
wirelessly transferring energy from an external energizer to a receiver implanted in a mammal patient's body,
sending feedback information from the receiver to the external energizer, the feedback information being related to the transfer of energy to the receiver, the feedback communication system being adapted to communicate the feed back information using the patient's body as an electrical capacitive conducting signal line,
providing the two dividing plates or portions on the sending side with signals which are the inverse of each other, when transmitting a signal through the capacitor, such that the first dividing plate or portion can be provided with a direct signal and the second dividing plate can be provided with an inverted signal, and
inverting the signals supplied by the inverter circuit for the communicating with the outside capacitor plate, one dividing plate or portion of the external capacitor plate being provided with the direct signal and the other dividing plate or portion being provided with the inverted signal.

16. The method according to claim 15, further comprising following over time a first energy balance between the amount of energy transferred to the receiver and the energy used by the medical implant,
in the step of sending the feedback information, sending information related to the first energy balance.

17. The method according to claim 15, further comprising following over time a second energy balance between the amount of energy received in the receiver and the amount of wireless energy transmitted from the external energizer,
in the step of sending the feedback information, sending information related to the transferred amount of energy, and
moving the external energizer along the patient's skin to reach a position where the second energy balance is optimized for a maximum energy transfer to the receiver.

18. The method according to claim 15, wherein, in sending the feedback information, a communication path is established between the receiver and the energizer using a capacitive coupling, so that the feedback information is sent using the capacitive coupling.

19. The method according to claim 15, wherein
the energizer comprises a feedback receiver in turn comprising a capacitive energy storage, and
the feedback information, transmitted using the capacitive coupling, is represented by electrical currents injected into or drawn from the capacitive energy storage.

\* \* \* \* \*